United States Patent [19]

Kawai et al.

[11] Patent Number: 4,943,532

[45] Date of Patent: Jul. 24, 1990

[54] ALKALI-RESISTANT CELLULASES AND MICROORGANISMS CAPABLE OF PRODUCING SAME

[75] Inventors: Shuji Kawai, Utsunomiya; Kazushi Oshino, Koshigaya; Hiromi Okoshi, Utsunomiya; Hajime Mori, Utsunomiya; Katsutoshi Ara, Utsunomiya; Susumu Ito, Utsunomiya; Kikuhiko Okamoto, Koshigaya, all of Japan

[73] Assignee: Kao Corporation, Tokyo, Japan

[21] Appl. No.: 126,739

[22] Filed: Nov. 30, 1987

[30] Foreign Application Priority Data

Dec. 5, 1986 [JP] Japan ............................. 61-289812
Dec. 8, 1986 [JP] Japan ............................. 61-292156
Dec. 9, 1986 [JP] Japan ............................. 61-293077
Dec. 9, 1986 [JP] Japan ............................. 61-293078
Jan. 27, 1987 [JP] Japan ............................. 62-16551
Jan. 27, 1987 [JP] Japan ............................. 62-16552
Jan. 27, 1987 [JP] Japan ............................. 62-16553
Aug. 3, 1987 [JP] Japan ............................. 62-194141

[51] Int. Cl.$^5$ ............................ C12N 9/42; C12R 1/07
[52] U.S. Cl. ................................ 435/209; 435/252.5; 435/832
[58] Field of Search ...................... 435/209, 252.5, 832

[56] References Cited

U.S. PATENT DOCUMENTS 3,983,002 9/1976 Ohya et al. ...................... 435/822

FOREIGN PATENT DOCUMENTS 269977 6/1988 European Pat. Off. .
271004 6/1988 European Pat. Off. .
2075028 11/1981 United Kingdom .
2095275 9/1982 United Kingdom .

OTHER PUBLICATIONS

Agricultural and Biological Chemistry, vol. 50, No. 1, Jan., 1986, pp. 233–237; Y. Koide et al.: "Molecular Cloning of a Cellulase Gene from *Bacillus subtilis* and its Expression in *Escherichia Coli*".

Chemical Abstracts, vol. 103, 1985, p. 735, abstract no. 213316q, Columbus, Ohio, U.S.A.: A. G. Williams et al.: "The Production of Hemicellulose-Degrading Enzymes by *Bacillus macerans* in Anacrobic Culture" & Appl Micro Biol. Biotechnol. 1985, 22(5), 318,24.

Sippola et al., "Coproduction of Several Exoenzymes in *Bacillus Subtilis,*" *FEMS Microbiol. Lett.*, vol. 10, No. 4, pp. 303–306, 1981.

*Primary Examiner*—Robert A. Wax
*Attorney, Agent, or Firm*—Oblon, Spivak, McClelland, Maier & Neustadt

[57] ABSTRACT

Novel alkali-resistant cellulases which have an optimum pH at a neutral region and have a high relative activity in an alkaline region are produced by microorganisms belonging to the genus Bacillus and growing in neutral medium.

The cellulases suffer little inhibition by means of detergent ingredients such as surface active agents, proteinases and chelating agents. Therefore, they can be conveniently used as one of ingredients for detergent compositions.

20 Claims, 12 Drawing Sheets pH for Reaction

Treating pH pH for Reaction

Treating pH

ALKALI-RESISTANT CELLULASES AND MICROORGANISMS CAPABLE OF PRODUCING SAME

BACKGROUND OF THE INVENTION

1. Field of the Invention

This invention relates to novel alkali-resistant cellulases and also to microorganisms which are able to produce the same.

2. Description of the Prior Art

The development of cellulases, which are cellulose-decomposing enzymes, has been made for the main purpose of effectively utilizing biomass resources and particularly, cellulose resources. A diversity of strains have been isolated as cellulase-producing fungi or bacteria including, for example, not only molds of the genera Aspergillus, Penicillium, Trichoderma, Fusarium, Humicola, Acremonium and the like, but also bacteria of the genera Pseudomonas, Cellulomonas, Ruminococcus, Bacillus and the like and actinomycetes of the genera Streptomyces, Thermoactinomyces and the like. At present, however, cellulases for biomass have not been frequently utilized on an industrial scale.

On the other hand, studies have been made on novel industrial utility of cellulases as an ingredient for detergents for clothes, to which attention has now been paid (Japanese Patent Publication Nos. 59-49279, 60-23158 and 60-36240). Most cellulases produced by microorganisms in the natural fields are classified as so-called neutral or acidic cellulases which exhibit optimum and stable enzymatic activity in a neutral to acidic range. Only a few cellulases are so-called alkaline cellulases which meet the requirements for formulation in detergent compositions for clothes or can exhibit a maximum activity in an alkaline pH range, and so-called alkali-resistant cellulases which have an alkali resistance. The term "alkaline cellulase" used herein is intended to mean one whose optimum pH is in an alkaline range, and the term "alkali-resistant cellulase" means one whose optimum pH is in a neutral to acidic range, but which has a satisfactory activity in an alkaline region as compared with an activity at an optimum pH and is maintained stable.

The term "neutral" means a pH range of from 6 to 8, and the term "alkaline" means a higher pH range.

For the production of alkaline cellulases and alkali-resistant cellulases usable in detergent compositions for clothes, only several methods have been proposed. These methods include, for example, a method of collecting cellulase A by cultivation of alkalophilic bacilli (Japanese Patent Publication No. 50-28515), a method of producing alkaline cellulase 301-A by cultivation of an alkalophilic bacterium belonging to the genus Cellulomonas (Japanese Patent Application Laid-open No. 58-224686), a method of producing carboxymethyl cellulase by cultivation of alkalophilic Bacillus No. 1139 (Fukumori, F., Kudo T. and Horikoshi, K., J. Gen. Microbiol., 131, 3339, (1985)), and a method of producing an alkaline cellulase by the use of one strain belonging to the genus Streptomyces (Japanese Patent Application Laid-open No. 61-19483). However, these methods are all unsuitable for the industrial fermentation production.

In recent years, we have found that Bacillus sp. KSM-635 (FERM BP-1485), which is one of alkalophilic bacteria, can efficiently produce alkaline cellulase K which is suitable as an ingredient for detergents for clothes and that proper selection of cultivation conditions enables one to enhance the productivity and conduct industrial fermentation production of the alkaline cellulase.

However, the cultivation conditions of the Bacillus sp. KSM-635 are not always advantageous from an industrial point of view. More particularly, an alkalophilic strain should be cultivated under alkaline pH conditions during the cultivation. A so-called alkaline fermentation process using alkalophilic strains has just been started, and a full knowledge on the physiological and biochemical properties of these alkalophilic microorganisms has not been obtained. Thus, difficulties have been involved in the preparation of media and the manner of cultivation sufficient to effect the industrial production by fermentation.

SUMMARY OF THE INVENTION

In order to solve the above problems, the present inventors made intensive studies in order to obtain neutral bacteria capable of producing either alkaline cellulases having an optimum pH in an alkaline region or alkali-resistant cellulases which can maintain high activity in an alkaline region as compared with the maximum activity at an optimum pH. To this end, these strains have been intensively searched for in natural fields while conducting a so-called gene recombination in which a strain growing in a neutral region is used as a host and a corresponding cellulase gene is cloned. As a result, it has been found that a series of microorganism belonging to the genus Bacillus can produce alkali-resistant cellulases although they grow in neutral media.

Typical alkali-resistant cellulases according to the invention have the following enzymatic properties:

(1) having an optimum pH of from 5 to 7;

(2) very stable and not inactivated at a pH of 5 to 10 with a residual activity of not less than 50% of the maximum activity being shown in the pH range of 4.5 to 11;

(3) the activity being inhibited by the presence of $Hg^{2+}$; and (4) the activity being rarely inhibited with proteinases, surface active agents and chelating agents.

DETAILED DESCRIPTION OF THE INVENTION AND PREFERRED EMBODIMENTS

Figure 1:
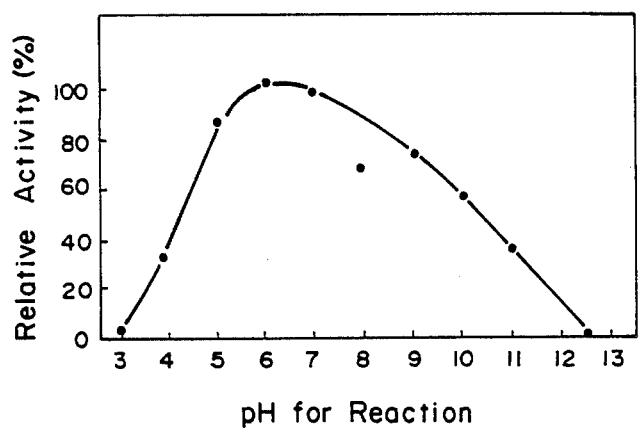
FIG. 1 is a graph showing the relation between a pH for the enzyme reaction of alkali-resistant cellulase K-534 and a relative activity.

Examples of the microorganism capable of producing the alkali-resistant cellulases of the invention include strains isolated by the present inventors from the solids of Haga-gun and Nikko-shi in Tochigi-ken, Japan, and deposited at the Fermentation Research Institute of Japan as Bacillus sp. KSM-534 (FERM BP-1508), Bacillus sp. KSM-344 (FERM BP-1506), Bacillus sp. KSM-539 (FERM BP-1509), Bacillus sp. KSM-577 (FERM BP-1510), Bacillus sp. KSM-588 (FERM BP-1513) and Bacillus sp. KSM-597 (FERM BP-1514).

These strains have the following mycological properties. It will be noted that the identification of the strains is carried out using the following media.

Medium 1: meat extract, 1.0; Bacto peptone, 1.0; NaCl, 0.5; Bacto agar, 1.5 (pH 7.2) (all indicated by wt% herein and hereinafter).

Medium 2: meat extract, 1.0; Bacto peptone, 1.0; NaCl, 0.5 (pH 7.2)

Medium 3: meat extract, 1.0; Bacto peptone, 1.0; NaCl, 0.5; gelatin, 1.0 (pH 7.2)

Medium 4: Bacto litmus milk, 10.0

Medium 5: Bacto peptone, 1.0; $KNO_3$, 0.1

Medium 6: Bacto peptone, 1.0; $NaNO_3$, 0.1

Medium 7: Bacto peptone, 0.7; NaCl, 0.5; glucose, 0.5 (pH 7.0)

Medium 8: Bacto peptone, 1.0

Medium 9: TSI agar (by Eiken Chem. Co., Ltd.); indicated amount

Medium 10: meat extract, 1.0; Bacto peptone, 1.0; NaCl, 0.5; soluble starch, 0.2; agar, 1.5

Medium 11: $NaNH_4HPO_4 \cdot 4H_2O$, 0.15; $KH_2PO_4$, 0.1; $MgSO_4 \cdot 7H_2O$, 0.02; sodium citrate, 0.25 (pH 6.8)

Medium 12 Christensen's medium (Eiken Chem. Co., Ltd.); indicated amount

Medium 13: glucose, 1.0; $KH_2PO_4$, 0.1; $MgSO_4 \cdot 7H_2O$, 0.05; KCl, 0.02; nitrogen sources, 0.1 (the nitrogen sources used were sodium nitrate and ammonium sulfate). (pH 7.2)

Medium 14: King A medium "Eiken" (Eiken Chem. Co., Ltd.); indicated amount

Medium 15: King B medium "Eiken" (Eiken Chem. Co., Ltd.); indicated amount

Medium 16: urea medium "Eiken" (Eiken Chem. Co., Ltd.); indicated amount

Medium 17: filter paper for cytochrome oxidase test (Nisshui Pharm. Co., Ltd.)

Medium 18: 3% hydrogen peroxide aqueous solution

Medium 19: OF basal medium (Difco Lab.); indicated amount

Medium 20: $(NH_4)_2HPO_4$, 0.1; KCl, 0.02; $MgSO_4 \cdot 7H_2O$, 0.02; yeast extract, 0.02; Bacto agar, 2.0; BCP (0.2% solution), 0.4

Medium 21: Bacto Sabouraud's dextrose agar medium (Difco Lab.); indicated amount Medium 22: meat extract, 0.3; Bacto peptone, 0.5; yeast extract, 1.0; glycerin, 2.0

Medium 23: phenyl alanine malonic acid salt medium (Nissui Pharm. Co., Ltd.); indicated amount Medium 24: skim milk, 5.0; Bacto agar, 1.5

Medium 25: meat extract, 0.3; Bacto peptone, 0.5; L-tyrosine, 0.5; Bacto agar, 1.5

Medium 26: Bacto peptone, 1.0; $NaNO_3$, 0.1

Medium 27: Simon's medium (Eiken Chem. Co., Ltd.); indicated amount (Mycological properties)

Bacillus sp. KSM-534:

(a) Results of Microscopic Observation

This is a bacillus having a size of the body of 0.4–0.8 micrometers × 1.5–6.0 micrometers, and has a cylindrical or ellipsoidal endospore (0.6–0.8 micrometers × 1.0–2.5 micrometers) at the center of the body. The bacillus has marginal flagella and is mobile. The Gram's staining is positive. Not aciduric.

(b) Growing State in Various Media (1) Meat broth agar plate culture (medium 1)

The growing state is weak. The colonies are in a round form with a smooth margin. The color tone of the colonies is light yellow, semi-transparent and glossy.

(2) Meat broth agar salnt culture (medium 1)

The growth is weak with the state being in a cloth-spreading form and being glossy, light yellow in color and semi-transparent.

(3) Meat broth liquid culture (medium 2)

Growing and becoming turbid.

(4) Meat broth gelatin stab culture (medium 3)

Growing in the surface layer with the gelatin being liquefied.

(5) Litmus milk medium (medium 4)

The liquefaction of the milk is recognized. A clear change of the litmus color is not recognized.

(c) Physiological Properties (1) The reduction and denitrification reactions of nitrates (media 5 and 6) are both negative.

(2) MR test (medium 7)
Whether the test is negative or positive is not clear (pH 5.2).
(3) VP test (medium 7)
Whether negative or positive is not clear (pH 5.2).
(4) Formation of indole (medium 8)
Negative.
(5) Formation of hydrogen sulfide (medium 9)
Nagative.
(6) Hydrolysis of starch (medium 10)
Positive.
(7) Utility of citric acid (media 11, 12)
Positive both in a Koser's medium and in a Christensen's medium.
(8) Utility of inorganic nitrogen sources (medium 13)
The nitrate and ammonium salt are both utilized.
(9) Formation of pigment (media 14, 15)
Negative.
(10) Urease (medium 16)
Negative.
(11) Oxidase (medium 17)
Positive.
(12) Catalase (medium 18)
Positive.
(13) Temperature and pH ranges for growth (medium 2)
The temperature range for growth is 15°–50° C and an optimum temperature range is 25°–40° C.
The pH range for the growth is 5–11 and an optimum pH range is 6–10.
(14) Behavior to oxygen
Facultatively anaerobic.
(15) 0-F test (medium 19)
Growing up aerobically or anaerobically with a gas generated.
(16) Utility of sugars (medium 20) (+:utilizing. —: not utilizing)

|   |   |   |
|---|---|---|
| 1. | L-arabinose | ± |
| 2. | D-xylose | − |
| 3. | D-glucose | + |
| 4. | D-mannose | − |
| 5. | fructose | + |
| 6. | D-galactose | + |
| 7. | maltose | + |
| 8. | sucrose | + |
| 9. | lactose | + |
| 10. | trehalose | − |
| 11. | D-sorbitol | + |
| 12. | D-mannitol | − |
| 13. | inositol | + |
| 14. | glycerin | + |
| 15. | starch | + |

(17) pH in VP medium (medium 7)
pH 5.2
(18) Growth in salt-containing media modified (medium 1)
Growing at 5%.
Growing at 7%.
Not growing at 10%.
(19) Growth at a pH of 5.7 (medium 21)
Growing.
(20) Formation of dihydroxyacetone (medium 22)
Negative.
(21) Deamination of phenylalanine (medium 23)
Negative.
(22) Decomposition of casein (medium 24)
Positive.
(23) Decomposition of tyrosine (medium 25)
Negative.
Bacillus sp. KSM-344:
(a) Results of microscopic observation
This is a bacillus having a size of the body of 0.6–0.8 micrometers×1.5–6.5 micrometers, making a cylindrical or ellipsoidal endospore (0.6–1.2 micrometers×2.0–4.0 micrometers) at the center of the body. It has no flagella and is mobile. The Gram staining is positive. Not aciduric.
(b) Growing state in various media
(1) Meat broth agar plate culture (medium 1)
The growing state is moderate. The shape of the colonies is circular or irregular with a smooth or rough surface and a smooth or wavy margin. The color tone of the colonies is white, and the colonies are semi-transparent and the gloss is rather dull.
(2) Meat broth agar slant culture (medium 1)
The growth is moderate and its state is in a cloth-spread form and is glossy, white in color and semi-transparent.
(3) Meat broth liquid culture (medium 2)
Growing. Although growing in the surface is not recognized, growing in the upper layer is recognized.
(4) Meat broth gelatin stab culture (medium 3)
Growing in the surface portion. The liquefaction of gelatin is recognized.
(5) Litmus milk culture (medium 4)
The liquefaction of the milk is recognized, but the color of litmus does not undergo any clear change.
(c) Physiological properties
(1) Reduction and denitrification reactions of nitrates (media 5, 6)
The reduction of the nitrate is positive and the denitrification is negative.
(2) MR test (medium 7)
Whether the test is negative or positive is not clear (pH 5.2).
(3) VP test (medium 7)
Whether negative or positive is not clear (pH 5.2).
(4) Formation of indole (medium 8)
Negative.
(5) Formation of hydrogen sulfide (medium 9)
Negative.
(6) Hydrolysis of starch (medium 10)
Positive.
(7) Utility of citric acid (media 11, 12)
Positive both in a Koser's medium and in a Christensen's medium.
(8) Utility of inorganic nitrogen sources (medium 13)
Utilizing both the nitrate and ammonium salt.
(9) Formation of pigment (media 14, 15)
Negative.
(10) Urease (medium 16)
Negative.
(11) Oxidase (medium 17)
Positive.
(12) Catalase (medium 18)
Positive.
(13) Temperature and pH ranges for growth (medium 2)
The temperature range for the growth is 15°–50° C and an optimum temperature range is 25°–40° C.
The pH range for the growth is 5–9 and an optimum pH range is 6–9.
(14) Behavior to oxygen
Facultatively anaerobic.
(15) 0-F test (medium 19)

Growing up either aerobically or anaerobically while generating a gas.

(16) Utility of sugars (medium 20) (+: utilizing. —: not utilizing)

| | | |
|---|---|---|
| 1. L-arabinose | | + |
| 2. D-xylose | | + |
| 3. D-glucose | | + |
| 4. D-mannose | | + |
| 5. fructose | | + |
| 6. D-galactose | | + |
| 7. maltose | | + |
| 8. sucrose | | + |
| 9. lactose | | — |
| 10. trehalose | | + |
| 11. D-sorbitol | | + |
| 12. D-mannitol | | + |
| 13. inositol | | + |
| 14. glycerin | | + |
| 15. starch | | + |

(17) pH in VP medium (medium 7) pH 5.2
(18) Growth in salt-containing media (modified medium 1)
Growing at 5%.
Growing at 7%.
Growing at 10%.
(19) Growth at a pH of 5.7 (medium 21)
Growing.
(20) Formation of dihydroxyacetone (medium 22)
Negative.
(21) Deamination of phenylalanine (medium 23)
Negative.
(22) Decomposition of casein (medium 24)
Positive.
(23) Decomposition of tyrosine (medium 25)
Negative.

Bacillus sp. KSM-539:

(a) Results of microscopic observation

This is a bacillus having a size of the body of 0.4–0.8 micrometers × 1.5–6.5 micrometers, making a cylindrical or ellipsoidal endospore (0.6–0.8 micrometers × 1.0–2.5 micrometers) at the center of the body. It has flagella and is mobile. The Gram's staining is positive. Not aciduric.

(b) Growing state in various media (1) Meat broth agar plate culture (medium 1)

The growing state is poor. The shape of the colonies is circular with a smooth surface and a smooth margin. The color tone of the colonies is light yellow, and the colonies are semi-transparent and glossy.

(2) Meat broth agar slant culture (medium 1)

The growing state is poor. The growing state is in a cloth-spread form and glossy, and is light yellow and semi-transparent.

(3) Meat broth liquid culture (medium 2)
Growing weakly.

(4) Meat broth gelatin stab culture (medium 3)
Growing in the surface portion. The liquefaction of gelatin is recognized.

(5) Litmus milk culture (medium 4)

The liquefaction of milk is recognized. The litmus color does not undergo any clear change. (c) Physiological properties (1) Reduction and denitrification reactions of nitrates (media 5, 6)
Both negative.

(2) MR test (medium 7)

Whether the test is negative or positive is not clear (pH 5.2).

(3) VP test (medium 7)
Whether negative or positive is not clear (pH 5.2).

(4) Formation of indole (medium 8)
Negative.

(5) Formation of hydrogen sulfide (medium 9)
Negative.

(6) Hydrolysis of starch (medium 10)
Positive.

(7) Utility of citric acid (media 11, 12)
Positive both in a Koser's medium and in a Christensen's medium.

(8) Utility of inorganic nitrogen sources (medium 13)
Utilizing both the nitrate and ammonium salt.

(9) Formation of pigment (media 14, 15)
Negative.

(10) Urease (medium 16)
Negative.

(11) Oxidase (medium 17)
Positive.

(12) Catalase (medium 18)
Positive.

(13) Temperature and pH ranges for growth medium (2)

The temperature range for the growth is 15°–50° C and an optimum temperature range is 25°–40° C.

The pH range for the growth is 5–11 and an optimum pH range is 6–10.

(14) Behavior to oxygen
Facultatively anaerobic.

(15) O-F test (medium 19)
Growing both aerobically or anaerobically.

(16) Utility of sugars (medium 20) (+: utilizing. —: not utilizing)

| | | |
|---|---|---|
| 1. L-arabinose | | + |
| 2. D-xylose | | + |
| 3. D-glucose | | + |
| 4. D-mannose | | + |
| 5. fructose | | + |
| 6. D-galactose | | — |
| 7. maltose | | — |
| 8. sucrose | | + |
| 9. lactose | | + |
| 10. trehalose | | — |
| 11. D-sorbitol | | + |
| 12. D-mannitol | | + |
| 13. inositol | | + |
| 14. glycerin | | + |
| 15. starch | | + |

(17) pH in VP medium (medium 7) pH 5.2
(18) Growth in salt-containing media (modified medium 1)
Growing at 5%.
Growing at 7%.
Not growing at 10%.
(19) Growth at a pH of 5.7 (medium 21)
Growing.
(20) Formation of dihydroxyacetone (medium 22)
Negative.
(21) Deamination of phenylalanine (medium 23)
Negative.
(22) Decomposition of casein (medium 24)
Positive.
(23) Decomposition of tyrosine (medium 25)
Negative.

Bacillus sp. KSM-577:

(a) Results of microscopic observation

This is a bacillus having a size of the body of 0.4–0.8 micrometers×1.0–2.0 micrometers, making a cylindrical or ellipsoidal endospore (0.4–0.8 micrometers×0.8–1.2 micrometers) at the center of the body. It has marginal flagella and is mobile. The Gram's staining is positive. Not aciduric.

(b) Growing state in various media (1) Meat broth agar plate culture (medium 1)

The growing state is poor. The shape of the colonies is circular with a smooth surface and a smooth margin. The color tone of the colonies is light yellow, and the colonies are semi-transparent and glossy.

(2) Meat broth agar slant culture (medium 1)

The growing is poor, and the growing state is in a cloth-spread form and glossy, with light yellow in color and semi-transparency.

(3) Meat broth liquid culture (medium 2)

Growing. Especially, the growth in the upper layer is recognized.

(4) Meat broth gelatin stab culture (medium 3)

Growing in the surface portions. The liquefaction of gelatin is recognized.

(5) Litmus milk culture (medium 4)

The liquefaction of milk is recognized but the litmus color does not undergo any clear change.

(c) Physiological properties (1) Reduction and denitrification reactions of nitrates (media 5, 6)

Both negative.

(2) MR test (medium 7)

Whether negative or positive is not clear (pH 5.2).

(3) VP test (medium 7)

Whether negative or positive is not clear (pH 5.2).

(4) Formation of indole (medium (8)

Negative.

(5) Formation of hydrogen sulfide (medium 9)

Negative.

(6) Hydrolysis of starch (medium 10)

Positive.

(7) Utility of citric acid (media 11, 12)

Positive both in Koser's medium and Christensen's medium.

(8) Utility of inorganic nitrogen sources (medium 13)

Utilizing both the nitrate and ammonium salt.

(9) Formation of pigment (media 14, 15)

Negative.

(10) Urease (medium 16)

Negative.

(11) Oxidase (medium 17)

Positive.

(12) Catalase (medium 18)

Positive.

(13) Temperature and pH ranges for growth (medium 2)

The temperature range for the growth is 15°–50° C and an optimum temperature range is 25°–40° C.

The pH range for the growth is 5–11 and an optimum pH range is 6–10.

(14) Behavior to oxygen

Facultatively anaerobic.

(15) 0-F test (medium 19)

Growing both aerobically and anaerobically.

(16) Utility of sugars (medium 20) (+: utilizing, —: not utilizing)

| 1. L-arabinose | + |
|---|---|
| 2. D-xylose | + |
| 3. D-glucose | + |
| 4. D-mannose | — |
| 5. fructose | + |
| 6. D-galactose | — |
| 7. maltose | — |
| 8. sucrose | + |
| 9. lactose | — |
| 10. trehalose | — |
| 11. D-sorbitol | + |
| 12. D-mannitol | + |
| 13. inositol | — |
| 14. glycerin | + |
| 15. starch | + |

(17) pH in VP medium (medium 7)

pH 5.2

(18) Growth in salt-containing media (modified medium 1)

Growing at 5% Growing at 7%. Not growing at 10%.

(19) Growth at a pH of 5.7 (medium 21)

Growing.

(20) Formation of dihydroxyacetone (medium 22)

Negative.

(21) Deamination of phenylalanine (medium 23)

Negative.

(22) Decomposition of casein (medium 24)

Positive.

(23) Decomposition of tyrosine (medium 25)

Negative.

Bacillus sp. KSM-588:

(a) Results of microscopic observation

This is a bacillus having a size of the body of 0.8–1.0 micrometers×1.0–5.0 micrometers, making a oval or cylindrical endospore (0.8–1.0 micrometers×1.0–1.5 micrometers) at the end of the center of the body. It has not marginal flagella and is not mobile. The Gram's staining is positive. Not aciduric.

(b) Growing state in various media (1) Meat broth agar plate culture (medium 1)

The shape of the colonies is irregular with a coarse surface and a leaf-like and waved hair-shaped margin. The color tone of the colonies is milky white to whitish yellow, opaque and the colonies are in the form of a film.

(2) Meat broth agar slant culture (medium 1)

The growing is moderate, and the growing state is in a cloth-spread form. The colonies are milky white in color and opaque.

(3) Meat broth liquid culture (medium 2)

Growing.

(4) Meat broth gelatin stab culture (medium 3)

Growing in the surface portions. The liquefaction of gelatin is recognized.

(5) Litmus milk culture (medium 4)

The liquefaction of the milk is recognized but the litmus color suffers decoloration in the depth of the culture.

(c) Physiological properties (1) Reduction and denitrification reactions of nitrates (media 5, 6)

Positive with the respect to the reduction of the nitrate and negative with respect to the denitrification.

(2) MR test (medium 7)

Positive.

(3) VP test (medium 7)

Positive.

(4) Formation of indole (medium 8)
Negative.
(5) Formation of hydrogen sulfide (medium 9)
Negative.
(6) Hydrolysis of starch (medium 10)
Positive.
(7) Utility of citric acid (media 11, 12)
Positive in Christensen's medium and not clear in Koser's medium as to whether positive or negative.
(8) Utility of inorganic nitrogen sources (medium 13)
Utilizing both the nitrate and ammonium salt.
(9) Formation of pigment (media 14, 15)
Forming a water-soluble, yellow pigment in the King B medium.
(10) Urease (medium 16)
Positive.
(11) Oxidase (medium 17)
Positive.
(12) Catalase (medium 18)
Positive.
(13) Temperature and pH ranges for growth (medium 2)
The temperature range for the growth is 10°–50° C and an optimum temperature range is 20°–40° C.
The pH range for the growth is 5–9 and an optimum pH range is 6–8.
(14) Behavior to oxygen
Aerobic
(15) O-F test (medium 19)
Oxidation.
(16) Formation of an acid and a gas from sugars (medium 20) (+: forming, −: not forming)

| | | | |
|---|---|---|---|
| 1. L-arabinose | + | − | |
| 2. D-xylose | + | − | |
| 3. D-glucose | + | − | |
| 4. D-mannose | + | − | |
| 5. fructose | + | − | |
| 6. D-galactose | + | − | |
| 7. maltose | + | − | |
| 8. sucrose | + | − | |
| 9. lactose | + | − | |
| 10. trehalose | + | − | |
| 11. D-sorbitol | + | − | |
| 12. D-mannitol | + | − | |
| 13. inositol | + | − | |
| 14. glycerin | + | − | |
| 15. starch | + | − | |

(17) pH in VP medium (medium 7)
pH 5.4
(18) Growth in salt-containing media (modified medium 1)
Growing at 5%. Growing at 7%. Growing at 10%.
(19) Growth at a pH of 5.7 (medium 21)
Growing.
(20) Decomposition of casein (medium 24)
Positive.
Bacillus sp. KSM-597:
(a) Results of microscopic observation
This is a bacillus having a size of the body of 0.5–0.8 micrometers × 1.0–2.0 micrometers, making a oval endospore (0.5–0.8 micrometers × 1.0–1.2 micrometers) at the center of the body. It has flagella and is mobile. The Gram's staining is positive. Not aciduric.
(b) Growing state in various media
(1) Meat broth agar plate culture (medium 1)
The growing state is moderate. The shape of the colonies is circular with a smooth surface and a smooth or wavy margin. The colonies are light yellow in color, semi-transparent and rather dull in gloss.
(2) Meat broth agar slant culture (medium 1)
The growing is moderate, and the growing state is in a cloth-spread form. The colonies are glossy, milky white in color and semi-transparent.
(3) Meat broth liquid culture (medium 2)
Growing. The surface growth is recognized and the top layer growth is also recognized.
(4) Meat broth gelatin stab culture (medium 3)
The liquefaction of gelatin is recognized.
(5) Litmus milk culture (medium 4)
The liquefaction of the milk is recognized but the litmus pigment does not undergo any clear change.
(c) Physiological properties
(1) Reduction and denitrification reactions of nitrates (media 5, 6)
Negative with the respect to both the reduction of the nitrate and the denitrification.
(2) MR test (medium 7)
Positive.
(3) VP test (medium 7)
Positive.
(4) Formation of indole (medium 8)
Negative.
(5) Formation of hydrogen sulfide (medium 9)
Negative.
(6) Hydrolysis of starch (medium 10)
Negative.
(7) Utility of citric acid (media 11, 12, 27)
Negative in the Koser's and Simons' media and positive in Christensen's medium.
(8) Utility of inorganic nitrogen sources (medium 13)
Not utilizing both the nitrate and ammonium salt.
(9) Formation of pigment (media 14, 15)
Forming a yellow pigment in the King B medium.
(10) Urease (medium 16)
Negative.
(11) Oxidase (medium 17)
Whether negative or positive is not clear.
(12) Catalase (medium 18)
Positive.
(13) Temperature and pH ranges for growth (medium 2)
The temperature range for the growth is 10°–50° C and an optimum temperature range is 20°–40° C.
The pH range for the growth is 5–10.
(14) Behavior to oxygen
Aerobic.
(15) 0-F test (medium 19)
Growing only aerobically.
(16) Utility of sugars (medium 20) (+: utilizing, −: not utilizing)

| | |
|---|---|
| 1. L-arabinose | + |
| 2. D-xylose | + |
| 3. D-glucose | + |
| 4. D-mannose | + |
| 5. fructose | + |
| 6. D-galactose | + |
| 7. maltose | + |
| 8. sucrose | + |
| 9. lactose | − |
| 10. trehalose | + |
| 11. D-sorbitol | − |
| 12. D-mannitol | + |
| 13. inositol | + |
| 14. glycerin | + |

| -continued | |
|---|---|
| 15. starch | — |

(17) pH in VP medium (medium 7)
pH 5.0
(18) Growth in salt-containing media (modified medium 1)
Growing at 5%. Growing at 7%.
Growing at 10%.
(19) Growth at a pH of 5.7 (medium 21)
Growing.
(20) Deamination of phenylalanine (medium 23)
Negative.
(21) Decomposition of casein (medium 24)
Positive.

These strains are considered to be spore-forming microorganisms belonging to the genus Bacillus. The above mycological properties are compared by reference to Bergey's Mannual of Determinative Bacteriology, 8th edition and "The Genus Bacillus", in Agriculture Handbook No. 427 written by Ruth E. Gordon, Agricultural Research Service, U.S. Department of Agriculture, Washington D.C. (1973). As a result, it has been found that all the strains of the invention are considered to be microorganisms belonging to the genus Bacillus. The strains of the invention are apparently different from so-called alkalophilic microorganisms which have been recently reported by Horikoshi and Akiba ("Alkalophilic Microorganism", Japan Scientific Society Press (Tokyo), 1982). This is because the alkalophilic microorganisms grow in alkaline media having a pH not less than 8 and cannot grow up in a neutral or lower pH region, whereas the strains of the invention are able to grow in a weakly acidic to alkaline region (pH 5–11).

The comparison between the present strains and other known strains belonging to the genus Bacillus reveal that the species which is most analogous to the strains of KSM-534, KSM-344, KSM-539 and KSM-577 may be *Bacillus licheniformis*. However, the comparison between the strains of the present invention and known strains belonging to *Bacillus licheniformis* reveals that the KSM-534 strain is different from those known strains with respect to the utility of mannitol and xylose and the reducibility of nitrates and the KSM-539 and KSM-577 strains are different with respect to the reducibility of nitrates. In addition, the above known strains belonging to *Bacillus licheniformis* cannot produce at least alkaline-resistant cellulases, and thus the strains of the present invention are considered as novel strains.

The species which is most analogous to *Bacillus* sp. KSM-588 may be *Bacillus megaterium* or *Bacillus cereus*. The comparison between known strains belonging to the *Bacillus megaterium* and the strain of the invention demonstrates a difference in the MR and VP tests. Moreover, comparison between the KSM-588 and strains belonging to the *Bacillus cereus* reveals that there are differences in the anaerobic growth and the utility of sugars. In addition, the strains belonging to *Bacillus megaterium* and *Bacillus cereus* cannot produce at least alkali-resistant cellulases. Thus, the present strain is also considered as a novel strain.

The species which is most analogous to the *Bacillus* sp. KSM-597 strain may be *Bacillus pumilus*. However, the comparison between the known strains belonging to *Bacillus pumilus* and the present strain reveals that the known strains do not produce at least alakli-resistant cellulases. Thus, the KSM-597 is considered as a novel strain.

For obtaining alkali-resistant cellulases of the invention using these strains, the strain is inoculated into media and cultivated by a usual manner. The medium should preferably have suitable amounts of carbon and nitrogen sources to be utilized. These carbon and nitrogen sources are not critical. Examples of the nitrogen sources include inorganic compounds such as ammonium nitrate, ammonium sulfate, ammonium chloride, ammonium phosphate, sodium nitrate and the like, and corn gluten meal, soybean flour, corn steep liquor, casamino acid, yeast extract, Pharmamedia, sardine meal, meat extract, peptone, Hypro, Ajipower, corn soybean meal, coffee grounds, cotton seed oil cake, Cultivator, Amiflex, Ajipron, Zest, Ajix and the like. The carbon sources include, for example, plant fibers such as chaff, wheat-gluten bread, filter paper, ordinary papers, sawdust and the like, wasted theriac, invert sugar, CMC, Avicel, cellulose cotton, xylan, pectin and the like In addition, utilizable carbon sources include, for example, arabinose, xylose, glucose, fructose, galactose, maltose, sucrose, lactose, sorbitol, inositol, glycerin, soluble starch and the like, and utilizable organic acids include, for example, acetic acid, citric acid, and the like. Besides, phosphoric acid and inorganic salts such as of $Mg^{2+}$, $Ca^{2+}$, $Mn^{2+}$, $Zn^{2+}$, $Co^{2+}$, $Na^{30}$, $K^+$ and the like, and inorganic and organic trace nutrient sources may be appropriately added, if necessary An intended cellulase can be collected from the thus obtained culture product and purified according to ordinary techniques of collecting and purifying enzymes. More particularly, the cells can be removed from a culture broth or solution by ordinary solid-liquid separation techniques such as centrifugal separation, filtration and the like, thereby obtaining a crude enzyme solution. This crude enzyme solution may be used as it is, or may be separated by salting-out precipitation, ultrafiltration or the like to obtain a crude enzyme The crude enzyme is subsequently purified by crystallization by any known methods to obtain a purified enzyme.

Typical alkali-resistant cellulases obtained in this manner include, for example, those named as cellulase K-534, cellulase K-344, cellulase K-539, cellulase K-577, cellulase K-588 and cellulase K-597. The present invention is further illustrated by way of these cellulases. It will be noted that the enzyme activity is measured according to the following method using the following buffer solutions.

pH 3–8: McIlvaine buffer solution
pH 8–11: glycine-sodium hydroxide buffer solution
pH 12–13: potassium chloride-sodium hydroxide buffer solution Enzymatic activity measurement:
(1) CMCase activity
0.1 ml of an enzyme solution was added to 0.9 ml of a base solution comprising 10 mg of CMC (A-01L, by Sanyo Kokusaku Pulp Co., Ltd.) and 100,$\mu$mols of each of the buffer solutions (McIlvaine, phosphoric acid, glycine-NaOH and the like), followed by reaction at 30° C for 20 minutes. After completion of the reaction, the resulting reducing sugar was quantitatively determined according to the 3,5-dinitro-salicylic acid (DNS) method. More particularly, 1.0 ml of the DNS reagent was added to 1.0 ml of the reaction solution and heated for 5 minutes at 100° C for color development. After cooling, 4.0 ml of deionized water was added for dilution. The diluted solution was subjected to colorimetry using a wavelength of 535 nm. The enzyme strength was expressed as one unit which was an amount of the enzyme sufficient to produce a reducing sugar corresponding to 1 μmol of glucose under the above conditions for 1 minute.

(2) Decomposition activity of PNPC

A suitable amount of an enzyme was acted on 1.0 ml of a reaction solution containing 0.1μmol of PNPC (Sigma Co., Ltd.) and 100 μmols of a phosphate buffer solution (pH 7.0) at 30° C, to which 0.3 ml of 1M $Na_2CO_3$ and 1.7 ml of deionized water were added successively, followed by subjecting the resultant released p-nitrophenol to colorimetry at 400 nm. The enzyme strength was expressed as one unit which was an amount of the enzyme sufficient to release 1 μmol of p-nitrophenol under the above conditions for 1 minute (3) Decomposition activities of Avicel, cellulose powder and filter paper A suitable amount of an enzyme was added to 2.0 ml of a reaction solution containing 20 mg of Avicel (Merck Inc.) and 200 μmols of a phosphate buffer solution (pH 7.0), followed by shaking for reaction at 30° C at 250 r.p.m. After completion of the reaction, the solution was cooled and centrifugally separated (5° C, 3000 r.p.m., 20 minutes), and 1.0 ml of the resultant supernatant liquid was subjected to quantitative determination of reducing sugar according to the 3,5-dinitro-salicylic acid (DNS) method. The above procedure was repeated for a cellulose powder decomposition activity using cellulose powder (Toyo Filter Paper Co., Ltd.) and for a filter paper decomposition activity using a filter paper (filter paper for examination of the cellulase activity, Toyo No. 51-specific). The enzyme strength was expressed by one unit which was an amount of the enzyme sufficient to produce reducing sugar corresponding to 1 μmol of glucose under the above conditions for 1 minute.

(4) Cellobiase activity

A suitable amount of an enzyme was acted on 1.0 ml of reaction solution containing 10 mg of cellobiose (Kanto Chem. Co., Ltd.) and 100 μmols of a phosphate buffer solution (pH 7.0) for an appropriate time, and then treated at 100° C for 2 minutes, thereby inactivating the enzyme. Thereafter, the amount of the resultant glucose was measured by the Mutarotase-GOD method (glucose C-test, Wako Junyaku Ind Co., Ltd ). The enzyme strength was expressed by one unit which was an amount of the enzyme sufficient to produce 2 μmols of glucose under the above conditions for 1 minute.

(Enzymatic Properties)

Cellulase K-534

(1) Action

Acting well on cellulosic materials such as cellulose, filter paper, Avicel, CMC and the like and causing them to be dissolved, thereby producing reducing sugars such as glucose (2) Substrate specificity This enzyme has activity not only on CMC, but also on cellulose powder, Avicel, filter paper and PNPC.

(3) Working pH and optimum pH

The working pH ranges very widely from 3 to 12.5 and the optimum pH is about 6 5. In a range of 4.5 to 10.5, the relative activity is not less than 50% of the activity at the optimum pH. Accordingly, this enzyme is believed to exhibit a satisfactory activity at the widest working pH range of from acidic to alkaline sides among cellulases studied up to now (FIG. 1).

(4) pH stability

Figure 2:
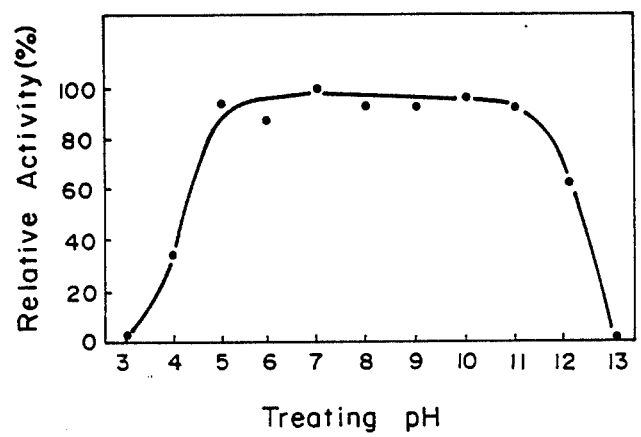
FIG. 2 is a graph showing the relation between a treating pH for the above enzyme and a residual activity.

The residual activity was measured after keeping the enzyme at different pHs at 30° C for 1 hour to determine the pH stability. As a result, it was found that the enzyme was very stable and was not inactivated at a pH of 5 to 11. In a pH of from 4.5 to 12.5, an activity of about 50% or over was maintained. Thus, the present enzyme is satisfactorily stable in a high alkaline region (FIG. 2).

(5) Optimum temperature

Figure 3:
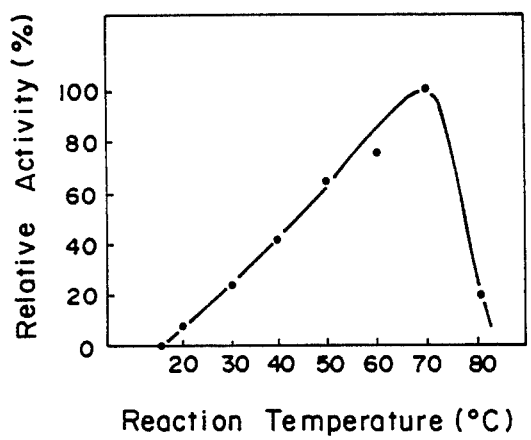
FIG. 3 is a graph showing the relation between a reaction temperature for the above enzyme and a relative activity.

The working temperature was in a wide range of from 15° to 85° C and the optimum temperature was found to be about 70° C. In a temperature range of from 45° to 75° C, the activity was 50% or higher of the activity at the optimum temperature (FIG. 3).

(6) Temperature stability

Figure 4:
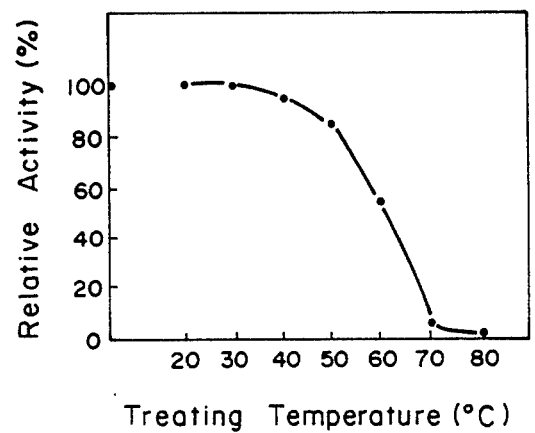
FIG. 4 is a graph showing the relation between a treating temperature for the above enzyme and a residual activity.

After treatment at the optimum pH for 30 minutes at different temperatures, the residual activity was measured. As a result, it was found that it was stable at 40° C and a residual activity of about 50% was obtained at 65° C (FIG. 4).

(7) Molecular weight

The molecular weight of the present enzyme was measured according to the gel filtration method using Sephadex G-100, with the result that main peaks were observed at about 15,000 and 30,000.

(8) Influences of metal ions

The present enzyme was subjected to determination of influences of various metal ions ($Al^{3+}$, $Fe^{3+}$, $Ba^{2+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentration of the metal ions was 1 mM except the concentration of that $K^+$ or $Na^+$ was 50 mM). As a result, it was found that the activity was inhibited by $Hg^{2+}$, but was more enhanced by $Ba^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was treated with a 0.05% solution of each surface active agent at 30° C for 15 minutes and subjected to the measurement of activity. As a result, the activity was not inhibited by any surface active agents. In addition, the inhibition of the activity was not recognized when using sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance to these proteinases.

(11) Influences of chelating agents

Chelating agents such as EDTA, EGTA, citric acid, zeolite and STPP were allowed to coexist at the time of the measurement of the activity, with the result that little inhibition was recognized. Cellulase K-344:

(1) Action

Acting well on cellulosic materials such as cellulose, filter paper, Avicel, CMC and the like and causing them to be dissolved, thereby producing reducing sugars such as glucose.

(2) Substrate specificity

This enzyme has activity not only on CMC, but also on cellulose powder, Avicel, filter paper and PNPC.

(3) Working pH and optimum pH

Figure 5:
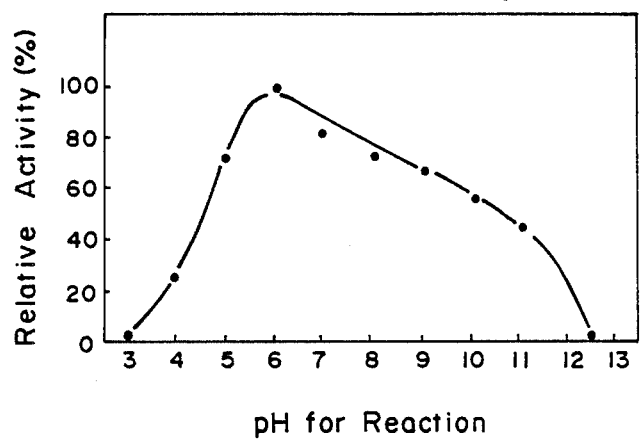
FIG. 5 is a graph showing the relation between a pH for the enzyme reaction of alkali-resistant cellulase K-344 and a relative activity.

The working pH ranges very widely from 3 to 12.5 and the optimum pH is 6. In a range of 4.5 to 11, the relative activity is not less than 50% of the activity at the optimum pH. Accordingly, this enzyme is believed to exhibit the widest working pH range in the alkaline side among cellulases which have ever been studied up to now (FIG. 5).

(4) pH stability

Figure 6:
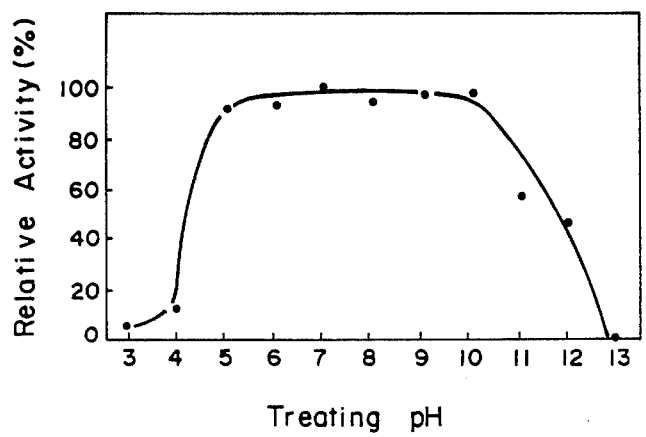
FIG. 6 is a graph showing a treating pH for K-344 and a relative activity.

The residual activity was measured after keeping the enzyme at different pHs at 30° C for 1 hour to determine the pH stability. As a result, it was found that the enzyme was very stable and was not inactivated at a pH of 5 to 10. In a pH of from 4.5 to 12, an activity of about 50% or over was maintained. Thus, the present enzyme is satisfactorily stable in a high alkaline region (FIG. 6).

(5) Optimum temperature

Figure 7:
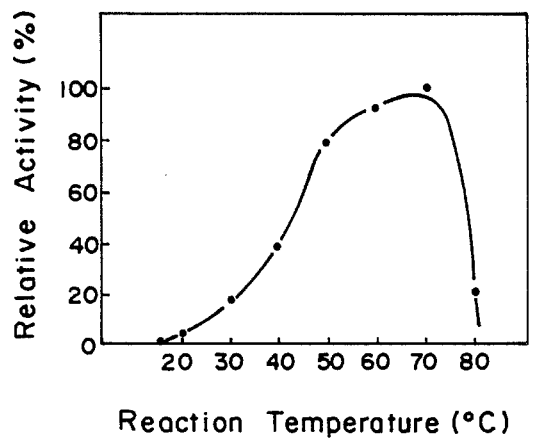
FIG. 7 is a graph showing a reaction temperature for K-344 and a relative activity.

The working temperature was in a wide range of from 15° to 80° C and the optimum temperature was found to be 70° C. In a temperature range of from 45° to 75° C, the activity was 50% or higher of the activity at the optimum temperature (FIG. 7).

(6) Temperature stability

Figure 8:
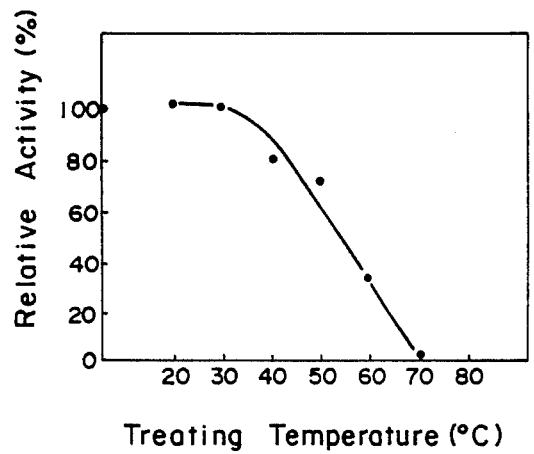
FIG. 8 is a graph showing a treating temperature for K-344 and a residual activity.

After treatment at the optimum pH for 30 minutes at different temperatures, the residual activity was measured. As a result, it was found that it was stable at 30° C and a residual activity of about 50% was obtained even at 55° C (FIG. 8).

(7) Molecular weight

The molecular weight of the present enzyme was measured according to the gel filtration method using Sephadex G-100, with the result that a primary peak was observed at about 16,000.

(8) Influences of metal ions

The present enzyme was subjected to determination of influences of various metal ions ($Al^{3+}$, $Fe^{3+}$, $Ba^{2+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentration of the respective metal ions was 1 mM except that the concentration of $K^{30}$ or $Na^+$ was 50mM).

As a result, it was found that the activity was inhibited by $Hg^{2+}$ and $Pb^{2+}$, but was more enhanced by $Co^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was treated with a 0.05% solution of each surface active agent at 30° C for 15 minutes and subjected to the measurement of the activity. As a result, it was found that the activity was not inhibited with any surface active agents. In addition, the inhibition of the activity was not recognized when using sodium dodecylsulfate which was a potential detergent.

(10) Proteinase resistance

Proteinases for detergents such as, for example, API-21 (Showa Denko Co.,Ltd.), Maxatase (Gist Co.,Ltd) and Alkalase (Novo Co., Ltd.), were allowed to coexist at the time of the measurement of the activity (0.1 Mg/ml) to determine their influences. It was found that the enzyme had a high resistance to these proteinases.

(11) Influences of chelating agents

Chelating agents such as EDTA, EGTA, citric acid, zeolite and sodium tripolyphsphate were allowed to coexist at the time of the measurement of the activity, with the result that little inhibition was recognized.

Cellulase K-539:

(1) Action

Acting well on cellulosic materials such as cellulose, filter paper, Avicel, CMC and the like and causing them to be dissolved, thereby producing reducing sugars such as glucose.

(2) Substrate specificity

This enzyme has activity not only on CMC, but also on cellulose powder, Avicel, filter paper and PNPC.

(3) Working pH and optimum pH

Figure 9:
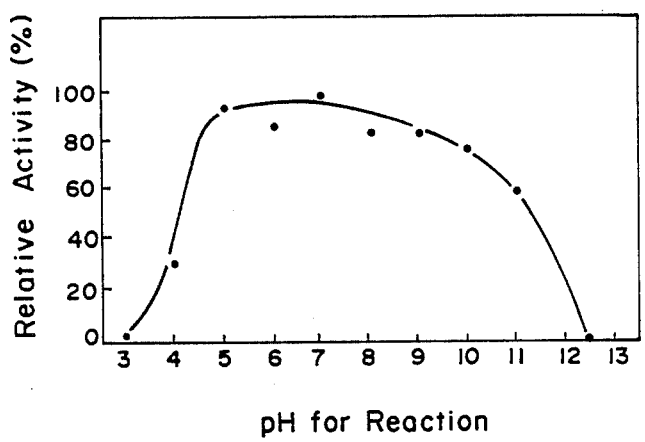
FIG. 9 is a graph showing the relation between a pH for the enzyme reaction of alkali-resistant cellulase K-539 and a relative activity.

The working pH ranges very widely from 3 to 12.5 and the optimum pH is 7. In a range of 4 to 11, the relative activity is not less than 50% of the activity in the optimum pH range. Accordingly, this enzyme is believed to exhibit the widest working pH range in the alkaline region among cellulases which have been ever studied up to now (FIG. 9).

(4) pH stability

Figure 10:
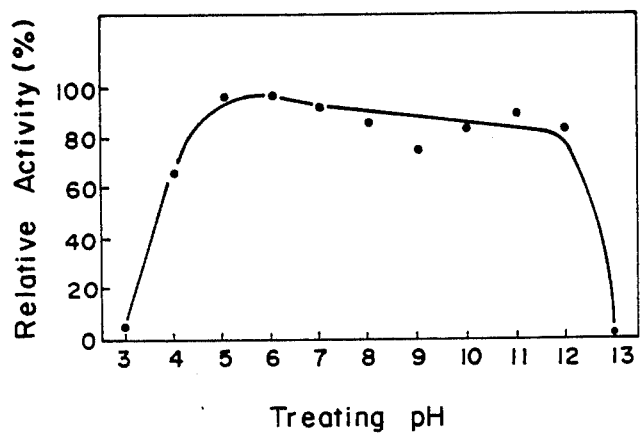
FIG. 10 is a graph showing the relation between a treating pH for K-539 and a residual activity.

The residual activity was measured after keeping the enzyme at different pHs at 30° C for 1 hour to determine the pH stability. As a result, it was found that the enzyme was very stable and was not inactivated at a pH of 5 to 12. In a pH of from 3.5 to 12.5, an activity of about 50% or over was maintained. Thus, the present enzyme is satisfactorily stable in a high alkaline region (FIG. 10).

(5) Optimum temperature

Figure 11:
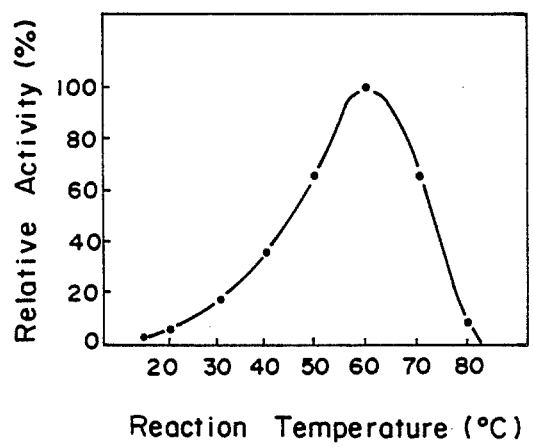
FIG. 11 is a graph showing the relation between a reaction temperature for K-539 and a relative activity.

The working temperature was in a wide range of from 15° to 85° C and the optimum temperature was found to be 60° C. In a temperature range of from 45° to 75° C, the activity was 50% or higher of the activity at the optimum temperature (FIG. 11).

(6) Temperature stability

Figure 12:
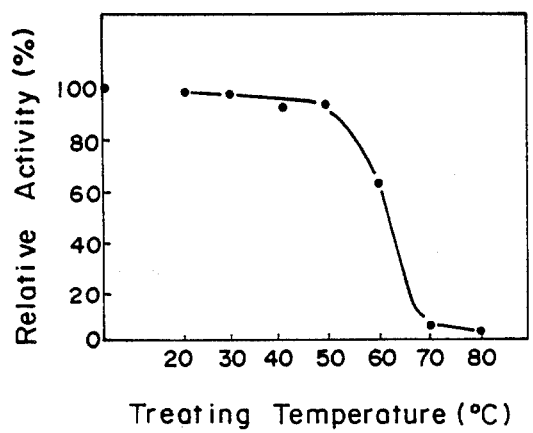
FIG. 12 is a graph showing the relation between a treating temperature for K-539 and a residual activity.

After treatment at the optimum pH for 30 minutes at different temperatures, the residual activity was measured. As a result, it was found that it was stable at 50° C and a residual activity of about 50% was obtained at 60° C (FIG. 12).

(7) Molecular weight

The molecular weight of the present enzyme was measured according to the gel filtration method using Sephadex G-100, with the result that major peaks were observed at about 18,000 and about 29,000.

(8) Influences of metal ions

The present enzyme was subjected to determination of influences of various metal ions ($AL^{3+}$, $Fe^{3+}$, $Ba^{2+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentration of the respective metal ions was 1 mM except that the concentration of $K^+$ or $Na^{30}$ was 50 mM).

As a result, it was found that the activity was inhibited by $Hg^{2+}$, but was more enhanced by $Ca^{2+}$, $Cd^{2+}$ and $Ba^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was treated with a 0.05% solution of each surface active agent at 30° C for 15 minutes and subjected to the measurement of the activity. As a result, the activity was rarely inhibited by any surface active agents. In addition, the inhibition of the activity was not recognized when using sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance to these proteinases.

(11) Influences of chelating agents

Chelating agents such as EDTA, EGTA, citric acid, zeolite and sodium tripolyphosphate were allowed to coexist at the time of the measurement of the activity, with the result that little inhibition was recognized.

Cellulase K-577:

(1) Action

Acting well on cellulosic materials such as cellulose powder, filter paper, Avicel, CMC and the like and causing them to be dissolved, thereby producing reducing sugars such as glucose.

(2) Substrate specificity

This enzyme has activity not only on CMC, but also on cellulose powder, Avicel and filter paper.

(3) Working pH and optimum pH

Figure 13:
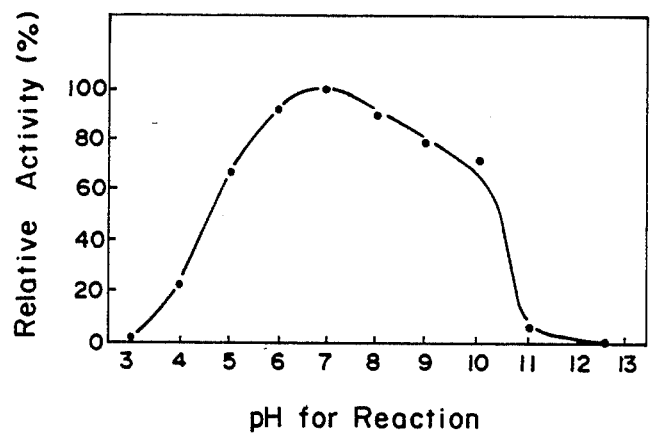
FIG. 13 is a graph showing the relation between a pH for the enzyme reaction of alkali-resistant cellulase K-577 and a relative activity.

The working pH ranges very widely from 3 to 12 and the optimum pH is 7. In a range of 4.5 to 10.5, the relative activity is not less than 50% of the activity in the optimum pH range. Accordingly, this enzyme is believed to exhibit the widest working pH range in the alkaline region among cellulases which have ever been studied up to now (FIG. 13).

(4) pH stability

Figure 14:
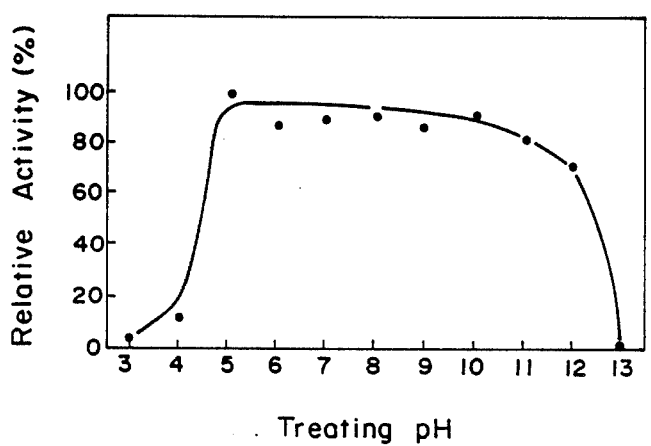
FIG. 14 is a graph showing the relation between a treating pH for K-577 and a residual activity.

The residual activity was measured after keeping the enzyme at different pHs at 30° C for 1 hour to determine the pH stability. As a result, it was found that the enzyme was very stable and was not inactivated at a pH of 5 to 12. In a pH of from 4.5 to 12.5, an activity of about 50% or over was maintained. Thus, the present enzyme is satisfactorily stable in a high alkaline region (FIG. 14).

(5) Optimum temperature

Figure 15:
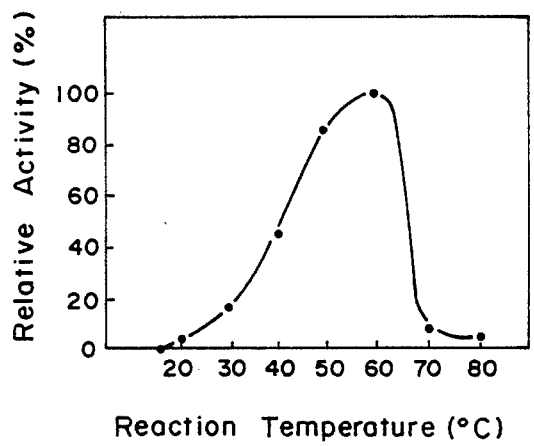
FIG. 15 is a graph showing the relation between a reaction temperature for K-577 and a relative activity.

The working temperature was in a wide range of from 15° to 75° C and the optimum temperature was found to be 60° C. In a temperature range of from 40° to 65° C, the activity was 50% or higher of the activity at the optimum temperature (FIG. 15).

(6) Temperature stability

Figure 16:
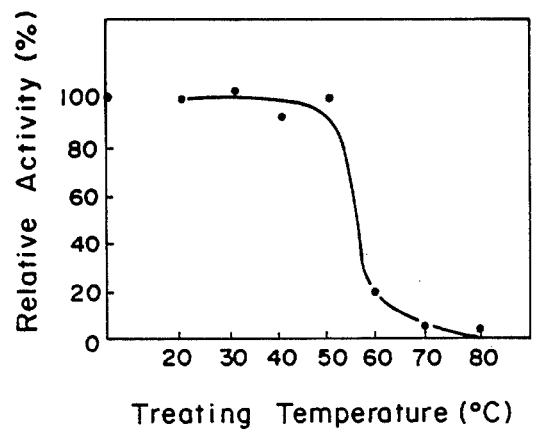
FIG. 16 is a graph showing the relation between a treating temperature for K-577 and a residual activity.

After treatment at the optimum pH for 30 minutes at different temperatures, the residual activity was measured. As a result, it was found that it was stable at 50° C and a residual activity of about 50% was obtained at 55° C (FIG. 16).

(7) Molecular weight

The molecular weight of the present enzyme was measured according to the gel filtration method using Sephadex G-100, with the result that major peaks were observed at about 17,000 and about 30,000, respectively.

(8) Influences of metal ions

The present enzyme was subjected to determination of influences of various metal ions ($Al^{3+}$, $Fe^{3+}$, $Ba^{2+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentration of the respective metal ions was 1 mM except that the concentration of $K^+$ or $Na^+$ was 50 mM).

As a result, it was found that the activity was inhibited by $Hg^{2+}$ and was more enhanced by $Ca^{2+}$, $Cd^{2+}$, $Ba^{2+}$ and $Co^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was treated with a 0.05% solution of each surface active agent at 30° C for 15 minutes and subjected to the measurement of the activity. As a result, it was found that the activity was rarely inhibited by any surface active agents. In addition, the inhibition of the activity was not recognized when using sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance of these proteinases.

(11) Influences of chelating agents

Chelating agents such as EDTA, EGTA, citric acid, zeolite and sodium tripolyphosphate were allowed to coexists at the time of the measurement of the activity, with the result that little inhibition was recognized.

Cellulase K-588:

(1) Action

Action well on cellulosic materials such as CMC and filter paper and causing them to be dissolved, thereby producing reducing sugars such as glucose.

(2) Substrate specificity

This enzyme has not only activity on CMC, but also activity on phosphoric acid-swollen cellulose, filter paper and PNPC.

(3) Working pH and optimum pH

Figure 17:
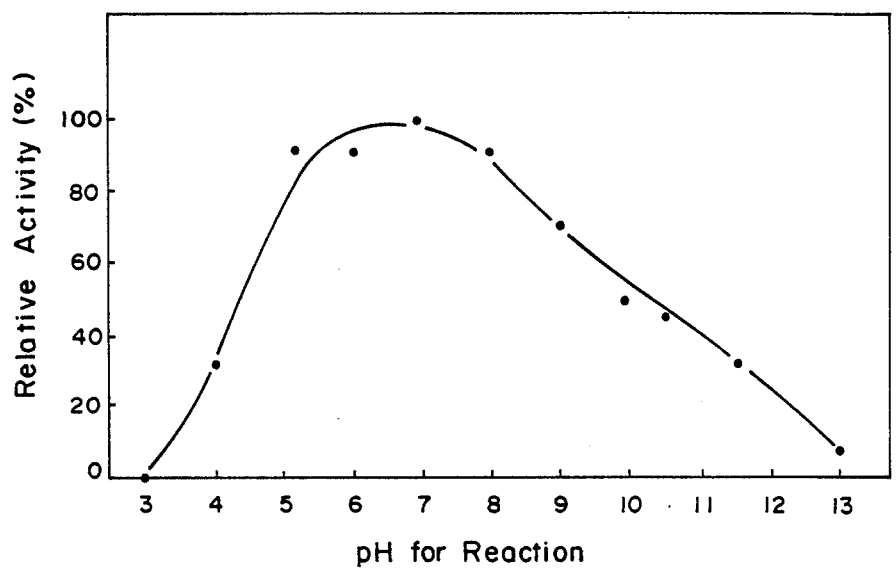
FIG. 17 is a graph showing the relation between a pH for the enzyme reaction of alkali-resistant cellulase K-588 and a relative activity.

The working pH ranges very widely from 3 to 13 and the optimum pH is 7. In a range of 4.5 to 10.5, the relative activity is not less than 50% of the activity at the optimum pH. Accordingly, this enzyme is believed to exhibit the widest working pH range in the alkaline region among cellulases which have ever been studied up to now (FIG. 17).

(4) pH stability

Figure 18:
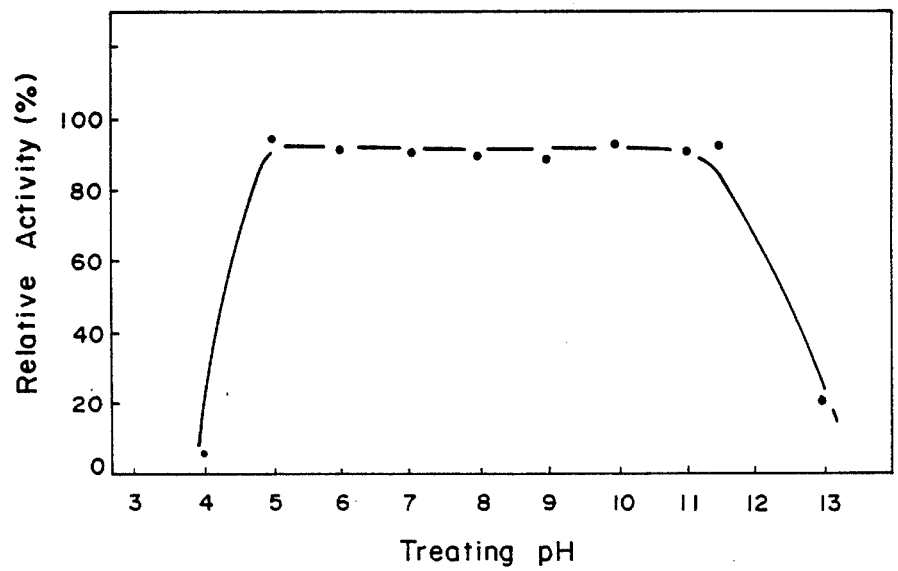
FIG. 18 is a graph showing the relation between a treating pH for K-588 and a residual activity.

The residual activity was measured after keeping the enzyme at different pHs at 30° C for 1 hours to determine the pH stability. As a result, it was found that the enzyme was very stable and was not inactivated at a pH of 5 to 11.5. In a pH of from 4.5 to 12.5, an activity of about 50% or over was maintained. Thus, the present enzyme is satisfactorily stable in a high alkaline region (FIG. 18).

(5) Optimum temperature

Figure 19:
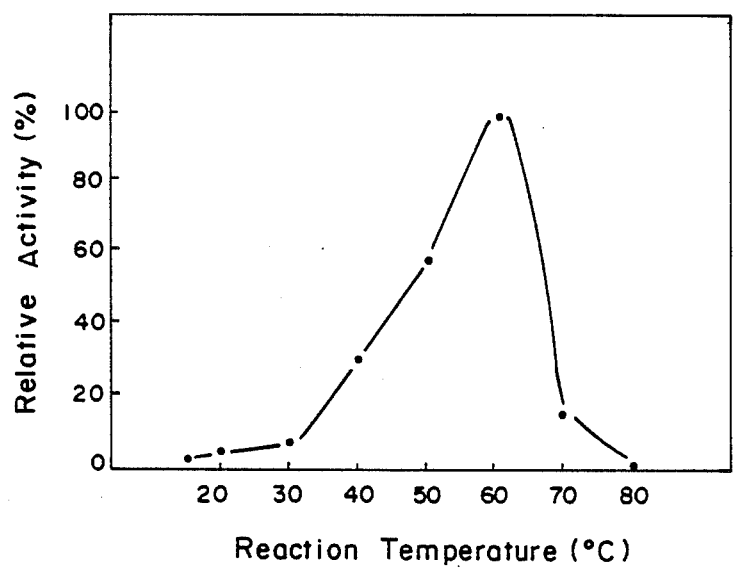
FIG. 19 is a graph showing the relation between a reaction temperature for K-588 and a relative activity.

The working temperature was in a wide range of from 15° to 80° C and the optimum temperature was found to be 60° C. In a temperature range of from 45° to 65° C, the activity was 50% or higher of the activity at the optimum temperature (FIG. 19).

(6) Temperature stability

Figure 20:
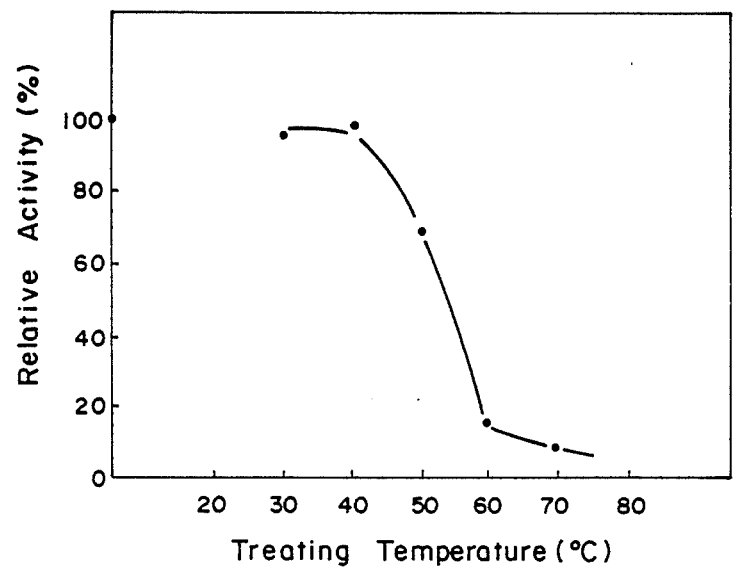
FIG. 20 is a graph showing the relation between a treating temperature for K-588 and a residual activity.

After treatment at the optimum pH for 30 minutes at different temperatures, the residual activity was measured. As a result, it was found that it was stable at 40° C and a residual activity of about 50% was obtained at 55° C (FIG. 20).

(7) Molecular weight

The molecular weight of the present enzyme was measured according to the gel filtration method using Bio-Gel P-150 (Bio-Rad Laboratories Co., Ltd.), with the result that major peaks were observed at about 27,000 and about 30,000, respectively.

(8) Influences of metal ions

The present enzyme was subjected to determination of influences of various metal ions ($Al^{3+}$, $Fe^{3+}$, $Ba^{2+}$, $Ca^{2+}$, $Cd^{2+}$, $Co^{2+}$, $Cr^{2+}$, $Cu^{2+}$, $Fe^{2+}$, $Hg^{2+}$, $Mn^{2+}$, $Mo^{2+}$, $Ni^{2+}$, $Pb^{2+}$, $Zn^{2+}$, $Li^+$, $K^+$, and $Na^+$) by permitting the ions to coexist at the time of the measurement of the activity (in which the concentration of the respective metal ions was 50 mM except that the concentration of $K^+$ or $Na^+$ was 50 mM).

As a result, it was found that the activity was inhibited by $Hg^{2+}$ and enhanced by $Fe^{2+}$ and $Mn^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was subjected to the measurement of the activity in 0.05% of a surface active agent. As a result, any significant influences of the surface active agents were not recognized. In addition, the inhibition of the activity was not recognized by means of sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist at the time of the measurement of the activity (0.1 mg/ml) to determine their influences. It was found that the enzyme had a high resistance to these proteinases.

(11) Influences of chelating agents

Chelating agents such as EDTA, EGTA, citric acid, zeolite and sodium tripolyphosphate were each allowed to coexist at the time of the measurement of the activity, with the result that no inhibition was recognized. Cellulase K-597:

For the measurement of the activity of the present enzyme, the following methods were used instead of the methods (3) and (4) described before, respectively.

(3-B) Decomposition activity for Avicel, cellulose powder, phosphoric acid-swollen cellulose, alkali-swollen cellulose and filter paper.

A suitable amount of an enzyme solution was added to 2.0 ml of a reaction solution containing 20 mg of Avicel (Merk Inc.) and 200 $\mu$mols of a phosphate buffer solution (pH 7.0), followed by shaking at 30° C at 250 r.p.m. After completion of the reaction, the reaction solution was cooled and centrifugally separated (5° C, 3000 r.p.m., 20 minutes) and 1 ml of the resultant supernatant liquid was subjected to quantitative determination of reducing sugar by the 3,5-dinitrosalicyclic acid (DNS) method. The above procedure was repeated using cellulose powder (Toyo Filter Paper Co., Ltd.) for the decomposition activity of the cellulose powder, celluloses treated by the Tomita et al method (Tomita et al, J. Ferment. Technol., 52, 235, 1974) for the activities of phosphoric acid-swollen cellulose and alkali-swollen cellulose, and filter paper (filter paper for examination of cellulase activity, Toyo No. 51-spec.) for the filter paper decomposition activity. The enzyme strength was expressed as follows: an amount of the enzyme sufficient to produce reducing sugar corresponding to 1 $\mu$mol of glucose under the above conditions for 1 minute was taken as one unit.

(4-B) Cellobiase activity

A suitable amount of an enzyme solution was added to a reaction solution containing 10 mg of cellobiose (Kanto Chem. Co., Ltd.) and 50 $\mu$mols of a phosphate buffer solution (pH 7.0) at 30° C for an appropriate time, followed by treatment at 100° C for 5 minutes to allow the enzyme to be inactivated. Thereafter, an amount of produced glucose was measured according to the Mutarotase-GOD method (glucose C-test, Wako Junyaku Ind. Co., Ltd.). The enzyme strength was expressed as follows: an amount of the enzyme sufficient to produce 2 $\mu$mol of glucose under the above conditions for 1 minute was taken as one unit.

(1) Action

Action well on cellulose materials such as cellulose, filter paper, Avicel, CMC and the like and causing them to be dissolved, thereby producing reducing sugars such as glucose.

(2) Substrate specificity

This enzyme has activity not only on CMC, but also on cellulose powder, Avicel, filter paper and PNPC.

(3) Working pH and optimum pH

Figure 21:
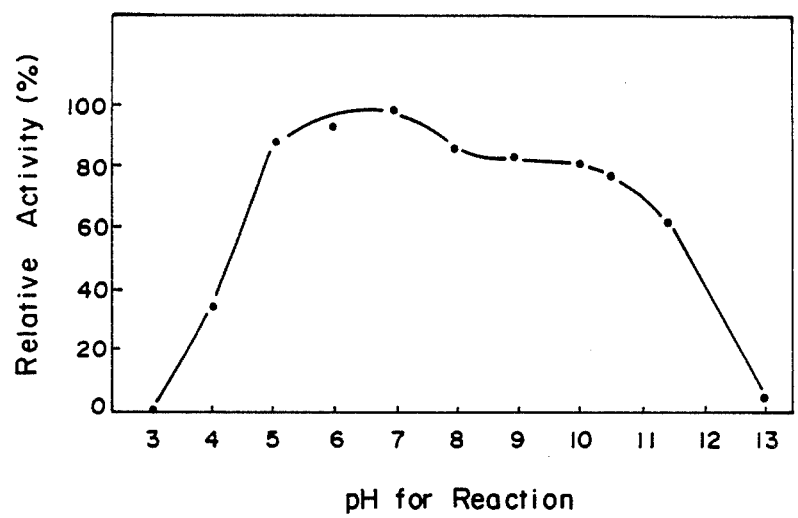
FIG. 21 is a graph showing the relation between a pH for the enzyme reaction of alkali-resistant cellulase K-597 and a relative activity.

The working pH ranges very widely from 3 to 13 and the optimum pH is 7. In a range of 4.5 to 11.5, the relative activity is not less than 50% of the activity at the optimum pH. Accordingly, this enzyme is believed to exhibit the widest working pH range in the alkaline region among cellulases which have ever been studied up to now (FIG. 21).

(4) pH stability

Figure 22:
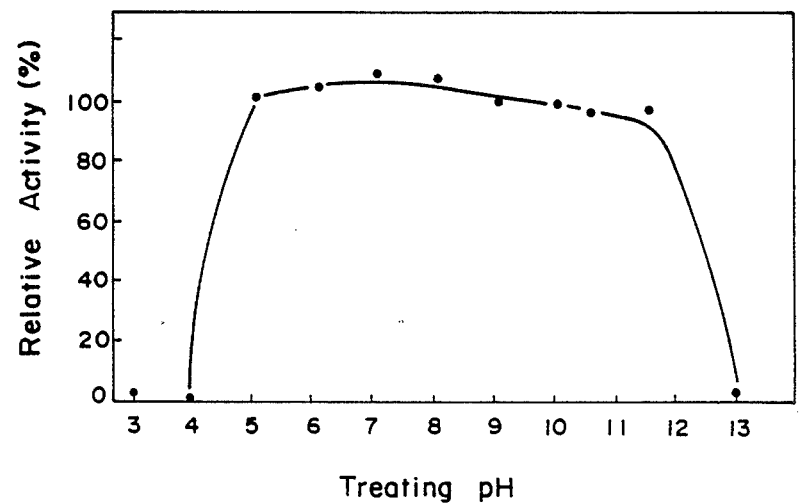
FIG. 22 is a graph showing the relation between a treating pH for K-597 and a residual activity.

The residual activity was measured after keeping the enzyme at different pHs at 30° C for 1 hours to determine the pH stability. As a result, it was found that the enzyme was very stable and was not inactivated at a pH of 5 to 11.5. In a pH of from 4.5 to 12.5, an activity of about 50% or over was maintained. Thus, the present enzyme is satisfactorily stable in a high alkaline region (FIG. 22).

(5) Optimum temperature

Figure 23:
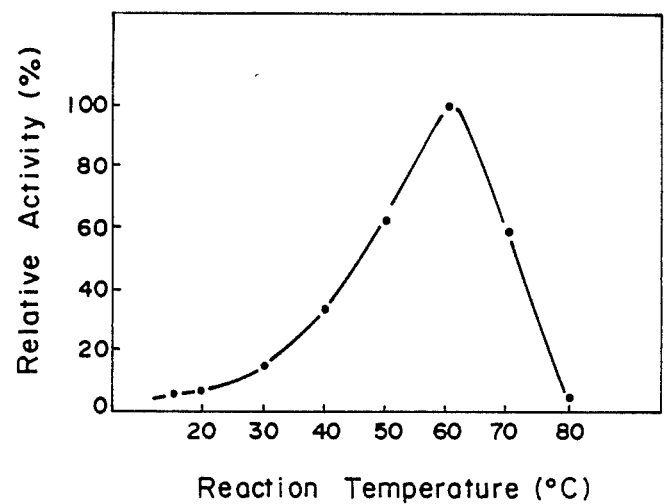
FIG. 23 is a graph showing the relation between a reaction temperature of K-597 and a relative activity.

The working temperature was in a wide range of from 15° to 80° C and the optimum temperature was found to be 60° C. In a temperature range of from 45° to 75° C, the activity was 50% or higher of the activity at the optimum temperature (FIG. 23). The measurement was effected at a pH of 6.

(6) Temperature stability

Figure 24:
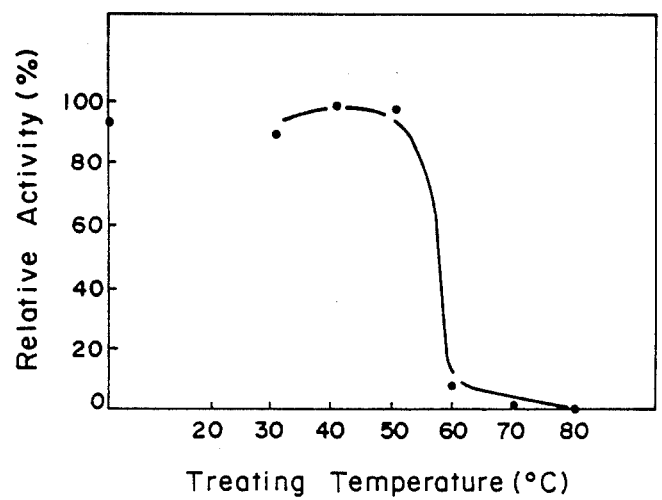
FIG. 24 is a graph showing the relation between a treating temperature for K-597 and a residual activity.

After treatment at a pH of 7 for 30 minutes at different temperatures, the residual activity was measured at pH of 6. As a result, it was found that it was stable at 50° C and a residual activity of about 50% was obtained at 55° C (FIG. 24).

(7) Molecular weight

The molecular weight of the present enzyme was measured according to the gel filtration method using Bio-Gel P-150 (Bio-Rad Laboratories Co., Ltd.), with the result that a major peak was observed at about 40,000.

(8) Influences of metal ions

The present enzyme was subjected to determination of influences of various metal ions ($Al^{3+}$, $Fe^{3+}$, $Ba^{2+}$, $Ca^{2+}$, $Cd^{2+}$, $Co^{2+}$, $Cu^{2+}$, $Fe^{2+}$, $Hg^{2+}$, $Mg^{2+}$, $Mo^{2+}$, $Ni^{2+}$, $Pb^{2+}$, $Zn^{2+}$, $K^+$, and $Na^+$) by permitting ions to coexist at the time of the measurement of the activity (in which the concentration of the respective metal ions was 1 mM except that the concentration of $K^+$ or $Na^+$ was 50 mM).

As a result, it was found that the activity was inhibited by $Hg^{2+}$ and enhanced by $Co^{2+}$.

(9) Influences of surface active agents

Influences of various surface active agents (e.g. LAS, AS, ES, AOS, alpha-SFE, SAS, soap and polyoxyethylene secondary alkyl ether) on the enzyme activity were determined. The present enzyme was subjected to the measurement of the activity in 0.05% of a surface active agent. As a result, any significant influences of the surface active agents were not recognized.

In addition, little inhibition of the activity was recognized when using sodium dodecylsulfate which was a potential detergent.

(10) Proteinase resistance

Proteinases for detergents such as, for example, API-21 (Showa Denko Co., Ltd.), Maxatase (Gist Co., Ltd.) and Alkalase (Novo Co., Ltd.), were allowed to coexist (0.1 mg/ml) at the time of the measurement of the activity to determine their influences. It was found that the enzyme had a high resistance to these proteinases.

(11) Influences of chelating agents

Chelating agents such as EDTA, EGTA, citric acid, zeolite and sodium tripolyphosphate were allowed to coexist at the time of the measurement of the activity, with the result that little inhibition was recognized.

The cellulases of the invention have an optimum pH at a neutral region, and have a high relative activity in an alkaline region and are stable. For example, cellulase K-534 has an optimum pH of 6.5, but is very stable over a pH range of from 5 to 11. Although cellulase K-344 has an optimum pH of 6, it has a relative activity of not less than 60% at a pH of 10 based on the activity at the optimum pH and is very stable in the pH range of from 5 to 10. Cellulase K-539 has an optimum pH of 7, but has a relative activity, at a pH of 10, of not less than 80% of the activity at the optimum pH and a relative activity, at a pH of 11, of not less than 60%. It is very stable in the pH range of from 5 to 12. Similarly, cellulase K-577 has an optimum pH of 7, but is very stable in the pH range of from 5 to 12. Moreover, cellulase K-588 has an optimum pH of 7, but has a relative activity, at a pH of 9, of not less than 70% of the activity at the optimum pH and a relative activity, at a pH of 10, of not less than 50% of the activity at the optimum pH. It is very stable in a wide pH range of from 5 to 11.5. Cellulase K-597 has an optimum pH of 7, but has a relative activity, at a high alkaline pH level of 11.5, of not less than 60% of the activity at the optimum pH and is very stable in a pH range of from 5 to 11.5.

All the cellulases suffer little inhibition by means of detergent ingredients such as surface active agents, proteinases and chelating agents. Accordingly, the enzymes of the present invention can be conveniently used as one of ingredients for detergent compositions.

Furthermore, the strains of the invention including Bacillus sp. KSM-534, KSM-344, KSM-539, KSM-577, KSM-588 and KSM-597 are variable under neutral conditions and can industrially produce corresponding alkali-resistant cellulases more easily than alkalophilic bacilli.

The present invention is described in more detail by way of the following examples.

EXAMPLE 1

A spoonful (about 0.5 g) of the soil obtained at Ichigai-machi, Haga-gun, Tochigi-ken, Japan was suspended in a sterilized physiological saline solution and thermally treated at 80° C for 10 minutes. The supernatant liquid of the thermally treated solution was appropriately diluted and applied to an agar medium for isolation (medium 1), followed by cultivation at 30° C for 3 days to form colonies. Colonies around which a transparent zone was formed on the basis of the dissolution of CMC were selected to collect CMCase producing bacilli. The thus collected microorganisms were inoculated into a liquid medium as medium 2 and subjected to shaking culture at 30° C for 3 days. After completion of the culture, a centrifugally separated supernatant liquid was obtained and subjected to measurement of the CMCase activity in a pH range of from 3 to 13 and also to screening of alkali-resistant cellulase-producing microorganism.

By the above procedure, there could be obtained Bacillus sp. KSM-534 strain (FERM BP-1508), Bacillus sp. KSM-344 strain (FERM BP-1506), Bacillus sp. KSM-539 (FERM BP-1509) and Bacillus sp. KSM-577 (FERM BP-1510).

Medium 1

| CMC | 2% |
|---|---|
| Polypeptone | 0.5% |
| Yeast extract | 0.05% |
| $KH_2PO_4$ | 0.1% |
| $Na_2HPO_4.12H_2O$ | 0.25% |
| $MgSO_4.7H_2O$ | 0.02% |
| Agar | 0.75% |
| pH 6.8 | |

Medium 2

| CMC | 1% |
|---|---|
| Polypeptone | 1% |
| Yeast extract | 0.5% |
| $KH_2PO_4$ | 0.1% |
| $Na_2HPO_4.12H_2O$ | 0.25% |
| $MgSO_4.7H_2O$ | 0.02% |
| pH 6.8 | |

EXAMPLE 2

The Bacillus sp. KSM-534 strain obtained in Example 1 was inoculated into the liquid medium 2 of Example 1, followed by shaking culture at 30° C for 3 days. After completion of the culture, the bacillus cells were centrifugally removed to obtain a crude enzyme solution. 3 liters of ethanol was added to 1 liter of the crude enzyme solution in dry ice/ethanol and the resultant precipitate was centrifugally removed, followed by freeze-drying to obtain 10 g of cellulase K-534 (specific activity of 3 units/g when determined at a pH of 9 herein and whenever it appears hereinafter) as a dry powder.

EXAMPLE 3

The general procedure of Example 2 was repeated except that, in the liquid medium 2, CMC was replaced by 1% sucrose and polypeptone was replaced by 7% corn steep liquor, and the shake culture was effected at 30° C for 2 days. The supernatant liquid obtained by centrifugal separation of the resultant culture solution was subjected to the measurement of the CMCase activity, with the result that the activity was 50 units/liter.

EXAMPLE 4

The Bacillus sp. KSM-344 strain obtained in Example 1 was cultivated and purified in the same manner as in Example 2, thereby obtaining as a dry powder 10.5 g of cellulase K-344 (specific activity of 6 units/g at a pH of 9).

EXAMPLE 5

The general procedure of Example 2 was repeated except that, in the liquid medium 2, CMC was replaced by 1% sucrose and polypeptone was replaced by 7% corn steep liquor, and that the Bacillus sp. KSM-344 was used for shake culture at 30° C for 2 days. The supernatant liquid obtained by centrifugal separation of the resultant culture solution was subjected to the measurement of the CMCase activity. As a result, it was found that the activity was 2900 units/liter.

EXAMPLE 6

The Bacillus sp. KSM-539 obtained in Example 1 was cultivated and purified in the same manner as in Example 2, thereby obtaining, as a dry powder, 9 g of cellulase K-539 (specific activity of 26 units/g at a pH of 9).

EXAMPLE 7

The general procedure of Example 2 was repeated except that, in the liquid medium 2, CMC was replaced by 1% sucrose and polypeptone was replaced by 7% corn steep liquor, and that the Bacillus sp. KSM-539 was used for shake culture at 30° C for 2 days. The supernatant liquid obtained by centrifugal separation of the resultant culture solution was subjected to the measurement of the CMCase activity. As a result, it was found that the activity was 40 units/liter.

EXAMPLE 8

The Bacillus sp. KSM-577 obtained in Example 1 was cultivated and purified in the same manner as in Example 2, thereby obtaining, as a dry powder, 9 g of cellulase K-577 (specific activity of 22 units/g at a pH of 9).

EXAMPLE 9

The general procedure of Example 2 was repeated except that, in the liquid medium 2, CMC was replaced by 1% sucrose and polypeptone was replaced by 7% corn steep liquor, and that the Bacillus sp. KSM-577 was used for shake culture at 30° C for 2 days. The supernatant liquid obtained by centrifugal separation of the resultant culture solution was subjected to the measurement of the CMCase activity. As a result, it was found that the activity was 40 units/liter.

EXAMPLE 10

A spoonful (0.5 g) of the soil obtained at Nikko-shi, Tochigi-ken, Japan was taken and suspended in a sterilized physiological saline solution, followed by repeating the procedure of Example 1, thereby obtaining a KSM-588 strain (FERM BP-1513) and a KSM-597 strain (FERM BP-1514) of the invention.

EXAMPLE 11

The Bacillus sp. KSM-588 obtained in Example 10 was cultivated and purified in the same manner as in Example 2, thereby obtaining, as a dry powder, 8 g of cellulase K-588 (specific activity of 5 units/g at a pH of 9).

EXAMPLE 12

The general procedure of Example 2 was repeated except that, in the liquid medium 2, CMC was replaced by 1% sucrose and polypeptone was replaced by 7% corn steep liquor, and that the Bacillus sp. KSM-588 was used for shake culture at 30° C for 2 days. The supernatant liquid obtained by centrifugal separation of the resultant culture solution was subjected to the measurement of the CMCase activity. As a result, it was found that the activity was 160 units/liter.

EXAMPLE 13

The Bacillus sp. KSM-597 strain obtained in Example 10 was cultivated and purified in the same manner as in Example 2, thereby obtaining, as a dry powder, 10 g of cellulase K-597 (specific activity of 8 units/g at a pH of 9).

EXAMPLE 14

The general procedure of Example 2 was repeated except that, in the liquid medium 2, CMC was replaced by 1% sucrose and polypeptone was replaced by 7% corn steep liquor, and that the Bacillus sp. KSM-597 was used for shake culture at 30° C for 3 days. The supernatant liquid obtained by centrifugal separation of the resultant culture solution was subjected to the measurement of the CMCase activity As a result, it was found that the activity was 300 units/liter.

What is claimed is:

1. A substantially pure alkali-resistant cellulase enzyme (K-534) having the following enzymatic properties:
   (1) action:
   acting well on cellulosic materials including carboxymethyl cellulose, cellulose, filter paper and microcrystalline cellulose causing them to be destroyed, thereby forming reducing sugars;
   (2) substrate specificity;
   having activity on carboxymethyl cellulose, cellulose powder, microcrystalline cellulose, filter paper and p-nitrophenyl cellobioside;
   (3) working pH and optimum pH:
   a working pH range from 3 to 12.5 and an optimum pH of about 6.5 with a relative activity of not less than 50% of the activity at an optimum pH being shown in the range of 4.5 to 10.5 ;
   (4) pH stability:
   very stable and not inactivated at a pH of 5 to 11 with an activity of not less than about 50% being maintained at a pH of 4.5 to 12.5;
   (5) optimum temperature:
   working temperature in a wide range of 15° to 85° C and an optimum temperature of about 70° C, in the range of 45° to 75° C, the activity is not less than 50% of the activity at the optimum temperature;
   (6) molecular weight:
   peaks for the molecular weight are at about 15,000 and about 30,000 (when determined by gel filtration).

2. A substantially pure alkali-resistant cellulase enzyme (K-344) having the following enzymatic properties:
   (1) action:
   acting on cellulosic materials including carboxymethyl cellulose, cellulose, filter paper and microcrystalline cellulose causing them to dissolved, thereby forming reducing sugars;
   (2) substrate specificity:
   having activity on carboxymethyl cellulose, cellulose powder, microcrystalline cellulose, filter paper and p-nitrophenyl cellobioside;
   (3) working pH and optimum pH:
   working pH from 3-12.5 and an optimum pH of 6 with a relative activity of not less than 50% of the activity at an optimum pH being shown in the range of 4.5 to 11;
   (4) pH stability:

very stable and not inactivate at a pH of 5 to 10 with an activity of not less than about 50% being maintained at a pH of 4.5 to 12;

(5) optimum temperature:

working temperature in a wide range of 15° to 80° C and an optimum temperature of 70° C, in the range of 40°–75° C, the activity is not less than 50% of the activity at the optimum temperature;

(6) molecular weight:

a peak for the molecular weight appears at about 16,000 (when determined by gel filtration).

3. A substantially pure alkali-resistant cellulose enzyme (K-539) having the following enzymatic properties:

(1) action:

acting well on cellulosic materials including carboxymethyl cellulose, cellulose, filter paper and microcrystalline cellulose causing them to be dissolved, thereby forming reducing sugars;

(2) substrate specificity:

having activity on carboxymethyl cellulose, cellulose powder, microcrystalline cellulose, filter paper and p-nitrophenyl cellobioside;

(3) working pH and optimum pH:

a working pH range of from 3 to 12.5 and an optimum pH of 7 with a relative activity of not less than 50% of the activity at the optimum pH being shown in the range of 4 to 11;

(4) pH stability:

very stable and not inactivated at a pH of 5 to 12 with an activity of not less than about 50% being maintained at a pH of 3.5 to 12.5;

(5) optimum temperature:

a working temperature in a wide range of 15° to 85° C and an optimum temperature of 60° C, in the range of 45° to 75° C, the activity is not less than 50% of the activity at the optimum temperature;

(6) molecular weight:

peaks for the molecular weight appear at about 18,000 and about 19,000, respectively (when determined by gel filtration);

(7) influences of metal ions:

inhibited by $Hg^{2+}$ and activated by $Ca^{2+}$, $Cd^{2+}$ and $Ba^{2+}$;

(8) influences of surface active agents:

little inhibition of activity by sodium linear alkylbenzensulfonates, sodium alkylsulfates, sodium polyoxyethylene alkylsulfates, sodium $\alpha$- olefin sulfonates, sodium $\alpha$- sulfonated aliphatic acid esters, sodium alkylsulfonates, soaps and polyoxyethylene secondary alkyl ethers;

(9) proteinase resistance:

resistant to proteinases; and

(10) influences of chelating agents:

ethylenediamine tetraacetic acid, ethylene glycol-bis-($\beta$-aminoethylether)-N,N,N', N''-tetraacetic acid, sodium tripolyphosphate, zeolite and citric acid do not inhibit activity.

4. A substantially pure alkali-resistant cellulase enzyme (K-577) having the following enzymatic properties:

(1) action:

acting well on cellulosic materials including carboxymethyl cellulose, cellulose, filter paper and microcrystalline cellulose causing them to be dissolved, thereby forming reducing sugars;

(2) substrate specificity:

having activity on carboxymethyl cellulose, cellulose powder, microcrystalline cellulose and filter paper;

(3) working pH and optimum pH:

a working pH range of from 3 to 12 and an optimum pH of 7 with a relative activity of not less than 50% of the activity at the optimum pH being shown in the range of 4.5 to 10.5;

(4) pH stability:

very stable and not inactivated at a pH of 5 to 12 with an activity of not less about 50% being maintained at a pH of 4.5 to 12.5;

(5) optimum temperature:

a working temperature in a wide range of from 15° to 75° C and an optimum temperature of 60° C, in the range of 40° to 65° C, the activity is not less than 50% of the activity at the optimum temperature;

(6) molecular weight:

peaks for the molecular weight appear at about 17,000 and about 30,000 (when determined by gel filtration;

(7) influences of metal ions:

inhibited by $Hg^{2+}$ and activated by $Ba^{2+}$, $Ca^{2+}$, $Cd^{2+}$ and $Co^{2+}$;

(8) influences of surface active agents:

little inhibition of activity by sodium linear alkylbenzensulfonates, sodium alkylsulfates, sodium polyoxyethylene alkylsulfates, sodium $\alpha$- olefin sulfonates, sodium $\alpha$- sulfonated aliphatic acid esters, sodium alkylsulfonates, soaps and polyoxyethylene secondary alkyl ethers;

(9) proteinase resistance:

resistant to proteinases; and

(10) influences of chelating agents:

ethylenediamine tetraacetic acid, ethylene glycol-bis-($\beta$-aminoethylether)-N,N,N', N''- tetraacetic acid, sodium tripolyphosphate, zeolite and citric acid do not inhibit activity.

5. A substantially pure alkali-resistant cellulase enzyme (K-588) having the following enzymatic properties:

(1) action:

acting well on cellulosic materials including carboxymethyl cellulose and filter paper and causing them to be dissolved, thereby forming reducing sugars;

(2) substrate specificity:

having activity on carboxymethyl cellulose, phosphoric acid-swollen cellulose, filter paper and p-nitrophenyl cellobioside;

(3) working pH and optimum pH:

a working pH in the range from 3 to 13 and an optimum pH of 7, with a relative activity of not less than 50% at the optimum pH being shown in the range of 4.5 to 10.5;

(4) pH stability:

very stable and not inactivated at a pH of 5 to 11.5 with an activity of not less about 50% being maintained at a pH of 4.5 to 12.5;

(5) optimum temperature:

a working temperature in a wide range of from 15° to 80° C and an optimum temperature of 60° C, in a range of 45° to 65° C, the activity is not less than 50% of the activity at the optimum temperature;

(6) molecular weight:

peaks for the molecular weight appear at about 27,000 and about 30,000 (when determined by gel filtration;

(7) influences of metal ions:

inhibited by $Hg^{2+}$;

(8) influences of surface active agents:
little inhibition of activity by sodium linear alkylbenzensulfonates, sodium alkylsulfates, sodium polyoxyethylene alkylsulfates, sodium α- olefin sulfonates, sodium α- sulfonated aliphatic acid esters, sodium alkylsulfonates, soaps and polyoxyethylene secondary alkyl ethers;

(9) proteinase resistance:
resistant to proteinases; and

(10) influences of chelating agents:
ethylenediaminetetraacetic acid and ethyleneglycol-bis-(β-aminoethylether)-N,N,N', N''- tetraacetic acid, sodium tripolyphosphate, zeolite and citric acid do not inhibit activity.

6. A substnatially pure alkali-resistant cellulase enzyme (K-597) having the following enzymatic properties:

(1) action:
acting well on cellulosic material including carboxymethyl cellulose, cellulose, filter paper and microcrystalline cellulose causing them to be dissolved, thereby forming reducing sugars;

(2) substrate specificity:
having activity on carboxymethyl cellulose, phosphoric acid-swollen cellulose, cellulose powder, microcrystalline cellulose, filter paper and p-nitrophenyl cellobioside;

(3) working pH and optimum pH:
a working pH range of from 3 to 13 and an optimum pH of 7, with a relative activity of not less than 50% of the activity at the optimum pH being shown in the range of 4.5 to 11.5;

(4) pH stability:
very stable and not inactivated at a pH of 5 to 11.5 with an activity of not less than 50% being maintained at a pH of 4.5 to 12.5;

(5) optimum temperature:
a working temperature in a wide range of from 15° to 80° C and an optimum temperature of 60° C, in the range of 45° to 75° C, the activity is not less than 50% of the activity at the optimum temperature;

(6) molecular weight:
a peak for the molecular weight appears at about 40,000 (when determined by gel filtration);

(7) influences of metal ions:
inhibited by $Hg^{2+}$ and activated by $Co^{2+}$;

(8) influences of surface active agents:
little inhibition of activity by sodium linear alkylbenzensulfonates, sodium alkylsulfates, sodium polyoxyethylene alkylsulfates, sodium α- olefin sulfonates, sodium α- sulfonated aliphatic acid esters, sodium alkylsulfonates, soaps and polyoxyethylene secondary alkyl ethers;

(9) proteinase resistance:
resistant to proteinases; and

(10) influences of chelating agents:
ethylenediamine tetraacetic acid, and ethylene glycol-bis-(β-aminoethylether)-N,N,N', N''- tetraacetic acid, sodium tripolyphosphate, zeolite and citric acid do not inhibit activity.

7. A biologically pure culture of Bacillus species KSM-534 deposited as FERM BP-1508 which is capable of producing the alkali-resistant cellulase of claim 1.

8. A biologically pure culture of Bacillus species KSM- 534 deposited as FERM BP-1506 which is capable of producing the alkali-resistant cellulase K-344 of claim 2.

9. A biologically pure culture of Bacillus species KSM- 539 deposited as FERM BP-1509 which is capable of producing the alkali-resistant cellulase K-539 of claim 3.

10. A biologically pure culture of Bacillus species KSM- 577 deposited as FERM BP-1510 which is capable of producing the alkali-resistant cellulase K-577 of claim 4.

11. A biologically pure culture of Bacillus species KSM- 588 deposited as FERM BP-1513 which is capable of producing the alkali-resistant cellulase K-588 of claim 5.

12. A biologically pure culture of Bacillus species KSM- 597 deposited as FERM BP-1514 which is capable of producing the alkali-resistant cellulase K-597 of claim 6.

13. A process of producing an alkali-resistant cellulase which is stable and not inactivated at a pH of 5 to 10 with a residual activity, at a pH of 4.5 to 11, of not less than 50% of a maximum activity, comprising: cultivating an alkali-resistant cellulase-producing bacterium selected from the group consisting of Bacillus species KSM-534 deposited as FERM BP-1508, Bacillus species KSM-344 deposited as FERM BP-1506, Bacillus species KSM 539 deposited as FERM BP -1509, Bacillus species KSM-577 deposited as FERM BP-1510, Bacillus species KSM-588 deposited as FERM BP- 1513 and Bacillus species KSM - 597 deposited as FERM BP-1514, which is capable of growing in a neutral medium, in a neutral medium, and collecting said alkali-resistant cellulase from the resulting culture product.

14. The process of claim 13, wherein the produced alkali-resistant cellulase has the following enzymatic properties:

(1) a wide optimum pH range of from 5 to 7;
(2) very stable and not inactivated at a pH of from 5 to 10 with a residual activity at a pH of 4.5 to 11 of not less than 50% of the maximum activity;
(3) activity being inhibited by the presence of $Hg^{2+}$; and
(4) activity being not inhibited by proteinases, surface acting agents and chelating agents.

15. The process of claim 13, wherein said bacterium is an alkali-resistant cellulase K-534-producing bacterium named Bacillus species KSM-534 deposited as FERM BP-1508.

16. The process of claim 13, wherein said bacterium is an alkali-resistant cellulase K-344-producing bacterium named Bacillus species KSM-344 deposited as FERM BP-1506.

17. The process of claim 13, wherein said bacterium is an alkali-resistant cellulase K-539-producing bacterium named Bacillus species KSM-539 deposited as FERM BP-1509.

18. The process of claim 13, wherein said bacterium is an alkali-resistant cellulase K-577-producing bacterium named Bacillus species KSM-577 deposited as FERM BP-1510.

19. The process of claim 13, wherein said bacterium is an alkali-resistant cellulase K-588-producing bacterium named Bacillus species KSM-588 deposited as FERM BP-1513.

20. The process of claim 13, wherein said bacterium is an alkali-resistant cellulase K-597-producing bacterium named Bacillus species KSM-597 deposited as FERM BP-1514.

* * * * *